(12) United States Patent
Russell et al.

(10) Patent No.: US 6,846,488 B2
(45) Date of Patent: Jan. 25, 2005

(54) CHIMERIC ANTIGEN-ENTEROTOXIN MUCOSAL IMMUNOGENS

(75) Inventors: Michael W. Russell, East Amberst, NY (US); Terry D. Connell, Williamsville, NY (US)

(73) Assignee: The UAB Research Foundation, Birmingham, AL (US)

( * ) Notice: Subject to any disclaimer, the term of this patent is extended or adjusted under 35 U.S.C. 154(b) by 131 days.

(21) Appl. No.: 09/825,105

(22) Filed: Apr. 3, 2001

(65) Prior Publication Data

US 2002/0004238 A1 Jan. 10, 2002

Related U.S. Application Data

(60) Provisional application No. 60/194,498, filed on Apr. 3, 2000.

(51) Int. Cl.[7] .................. A61K 39/00; A61K 38/00; C12N 15/74; C12P 21/08
(52) U.S. Cl. .................. 424/192.1; 424/184.1; 424/200.1; 424/236.1; 424/258.1; 424/282.1; 424/93.2; 435/320.1; 435/69.1; 435/69.7; 514/2; 514/44; 530/350; 530/387.3
(58) Field of Search .................. 514/44, 2; 435/320.1, 435/69.1, 69.7; 424/184.1, 200.1, 93.2, 192.1, 236.1, 258.1, 282.1; 530/350, 387.3

(56) References Cited

U.S. PATENT DOCUMENTS

| | | | |
|---|---|---|---|
| 5,656,488 A | | 8/1997 | Curtiss .................. 435/252.33 |
| 6,030,624 A | * | 2/2000 | Russell et al. .................. 424/200.1 |
| 6,110,898 A | * | 8/2000 | Malone et al. .................. 514/44 |

OTHER PUBLICATIONS

Immune Tolerance, PubMed, Mesh term database 2004.*
Schodel et al. Recognition of a hepatitis B virus nucleocapsid T–cell epitope expressed as a fusion protein with the subunit B of *Escherichia coli* heat labile enterotoxin in attenuated salmonellae 1990.*

Connell et al. Characterization of hybrid toxins produced in *escherichia coli* by assembly of A and B polypeptides from type I and type II heat–labile enterotoxins vol. 60 No. 4 pp. 1653–1661. Infection and Immunity, 1992.*

Rappuoli, et al. *Structure and Mucosal Adjuvanticity of Cholera and Escherichia coli Heat–Labile Interotoxins.* vol. 20, 1999, pp. 493–500.

Connell, et al. *Immunostimulatory Activity of LT–IIA, A Type II Heat–Labile Enterotoxin of Escherichia coli. Elsevier Science.* vol. 62, 1998, pp. 117–120.

Hajishengallis, et al. *Mucosal Immunization With a Bacterial Protein Antigen Genetically Coupled to Cholera Toxin A2/B Subunits. The Journal of Immunology,* vol. 154, pp. 4322–4332. 1995.

Hajishengallis, et al. *Persistence of Serum and Salivary Antibody Responses After Oral Immunization with a Bacterial Protein Antigen Genetically Linked to the A2/B Subunits of Cholera Toxin. Infection and Immunity,* vol. 64, pp. 665–667. 1996.

Toida, et al. *Oral Immunization With the Saliva–Binding Region of Streptococcus Mutans AGI/II Genetically Coupled to the Cholera Toxin B Subunit Elicits T–Helper–Cell Responses in Gut–Associated Lymphoid Tissues. Infection and Immunity,* vol. 65, pp. 909–915. 1997.

* cited by examiner

*Primary Examiner*—Q. Janice Li
(74) *Attorney, Agent, or Firm*—Benjamin Aaron Adler

(57) ABSTRACT

The present invention provides methods of inducing immune responses by recombinant antigen-enterotoxin chimeric mucosal immunogens that contain the A2/B subunits of cholera toxin or heat-labile type II toxins. These chimeric immunogens differentially enhance antibody secretion, cytokine production, as well as B7-dependent co-stimulation of T cells and CD40L expression on CD4[+] T cells.

10 Claims, 11 Drawing Sheets

66   (1)     (2)

45

Figures 1A, 1B, 1C:
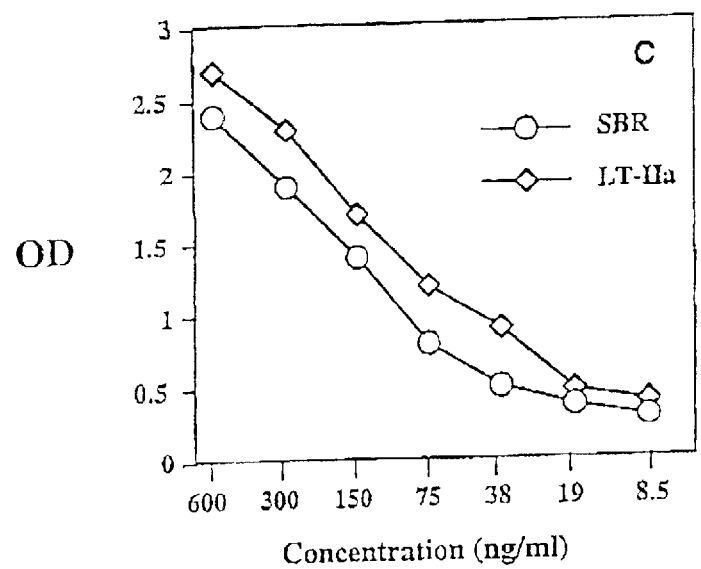

31
21
14

6.5

66   (1)     (2)     (3)     (4)

45

31
21
14

6.5

Immunogen

- ☐ Sham-immunized
- SBR
- SBR-CTA2/B
- SBR-LT-IIaA2/B

CHIMERIC ANTIGEN-ENTEROTOXIN MUCOSAL IMMUNOGENS

CROSS-REFERENCE TO RELATED APPLICATION

This non-provisional patent application claims benefit of provisional patent application U.S. Ser. No. 60/194,498, filed Apr. 3, 2000, now abandoned.

FEDERAL FUNDING LEGEND

This invention was produced in part using funds obtained through grants from the National Institutes of Health. Consequently, the federal government has certain rights in this invention.

BACKGROUND OF THE INVENTION

1. Field of the Invention

The present invention relates generally to the field of immunology. More specifically, the present invention relates to chimeric antigen-enterotoxin mucosal immunogens that differentially enhance immune responses.

2. Description of the Related Art

Cholera toxin (CT) produced by *Vibrio cholerae* and the labile toxins (LT) from *Escherichia coli* are structurally related heat-labile enterotoxins (HLE) that have been employed as mucosal adjuvants to augment mucosal immune responses to co-administered antigens (Ag) (1, 2). These enterotoxins consist of an ADP-ribosylating A1 subunit non-covalently coupled with a pentameric ring of five identical B subunits through the A2 subunit, which is the C-terminal end of the A polypeptide (3). Initial studies using heat-labile enterotoxins as adjuvants in animal models led to the conclusion that their adjuvanticity was due to their toxic enzyme activity (4). ADP-ribosylation of the Gsα subunit of adenylate cyclase results in abnormally high levels of intracellular cAMP (3, 5), and subsequent chloride ion efflux into the lumen of the gut that is ultimately responsible for the characteristic watery diarrhea.

Due to the toxic nature of the holotoxins, many investigators have tried to dissociate the toxicity associated with the A1-subunit from the adjuvanticity of the $AB_5$ complex, and have attempted to address the immunostimulatory effects of $B_5$ subunit receptor-mediated interactions. Earlier studies using commercial CTB preparations contaminated with intact CT made it impossible to distinguish between the adjuvanticity associated with ADP-ribosyltransferase activity and the binding properties of the $AB_5$ complex. This issue was further complicated by the synergistic effect of holotoxin on the adjuvanticity of the B subunit (6, 7). Experiments using a type I LT B subunit (LT-I B) mutant that lacks GM1-binding demonstrated that both immunogenicity and adjuvanticity were dependent upon receptor binding (8). Moreover, it has been demonstrated that upregulation of the co-stimulatory molecules, B7-1 and B7-2, on antigen-presenting cells (APC) by LT-I B or non-toxic derivatives of CT was abrogated when GM1 binding was blocked (9, 10). These studies demonstrate that GM1-$B_5$ subunit interactions are necessary for the adjuvanticity associated with LT-I B or CT. However, LT-I and the type II HLE bind a broader range of gangliosides than CT, and it is not known whether these add to or substitute for GM1 binding in the immunostimulatory properties displayed by these molecules.

Two types of heat-labile enterotoxin have been distinguished on the basis of distinct immunoreactivity (11, 12): type I heat-labile enterotoxins are represented by CT and LT-I (12, 13); type II heat-labile enterotoxins include *E. coli* LT-IIa and LT-IIb (14–17). Comparison of the predicted amino acid sequences reveals considerable variability between type I and type II enterotoxins (11, 12, 18, 19). This extensive diversity imparts different ganglioside-binding properties to the respective B subunits. The cellular receptor for CT has been shown to be the monosialoganglioside GM1 (20). The B subunit of LT-IIa binds with high affinity to GD1b and less strongly to GM1, GT1b, GD1b, GD2, GD1a and GM2. LT-IIb binds with high affinity to GD1a (20).

It has recently been shown that the type II heat-labile enterotoxins can serve as mucosal adjuvants that enhance Ab responses to a co-administered protein antigen (Ag) given by the intranasal (i.n.) route (21). However, it is not clear if the different response patterns observed were related to the more promiscuous binding activities of the B subunits of the LT-II toxins, compared to CT. In addition to an adjuvant effect for co-administered Ag, heat-labile enterotoxins are themselves excellent mucosal immunogens and elicit strong secretory IgA and circulating IgG Ab responses. This property has been exploited in the construction of potent mucosal immunogens by coupling protein Ags to the non-toxic B subunit of CT (22–24). Initially, proteins were coupled to CTB by chemical conjugation, but later a genetic strategy for fusing an antigenic polypeptide to the A2 subunit of CT and co-expressing this with CTB was devised, yielding a chimeric immunogen in the form of Ag-CTA2/B (24, 25). Given that LT-II and CT have distinct ganglioside-binding specificity and somewhat different adjuvant activity, it is postulated that a chimeric protein consisting of Ag-LT-IIA2/B would have advantageous immunogenic properties compared to those of a chimeric protein consisting of Ag-CTA2/B. Therefore, the purpose of the present study was to compare the mucosal immunogenicity of chimeric proteins composed of the same protein Ag genetically coupled in an identical manner to the A2/B subunits of CT or LT-II. Possible mechanisms that might account for differences in their immunogenic properties were also explored.

The prior art is deficient in an effective means of enhancing immune responses by chimeric antigen-enterotoxin mucosal immunogens. The present invention fulfills this long-standing need and desire in the art.

SUMMARY OF THE INVENTION

The present invention compares the ability of the non-toxic A2/B subunits of cholera toxin or the *Escherichia coli* heat-labile type II toxins (LT-II) to augment the immunogenicity of a genetically coupled protein antigen administered by a mucosal route. The enzymatically active A1 subunits of cholera toxin (CT), LT-IIa or LT-IIb were replaced with the saliva-binding region (SBR) from the streptococcal adhesin AgI/II. Intranasal immunization of BALB/c mice with the chimeric proteins induced significantly higher plasma and mucosal anti-SBR IgA and IgG antibody (Ab) responses. Moreover, SBR-CTA2/B strongly up-regulated B7-2 but not B7-1 expression. SBR-CTA2/B-treated B cells enhanced the proliferation of anti-CD3-stimulated CD4$^+$ T cells, and this proliferation was reduced by treatment with anti-B7-2 but not with anti-B7-1 or an isotype-control Ab. Thus, SBR-CTA2/B enhances antibody responses and induces differential expression of B7-2 that has co-stimulatory effects on T cells.

Induction of systemic and mucosal immune responses by CT and type II HLT was related to induction of distinct cytokine secretion profiles. These mucosal adjuvants were found to differentially induce cytokine production in anti- CD3-activated human peripheral blood mononuclear cells (PBMC). CT suppressed IL-2, TNF-α, and IL-12 production by PBMC cultures more than either LT-IIa or LT-IIb. CT, but not LT-IIa or LT-IIb, also significantly reduced the expression of CD40L on $CD4^+$ T cells. In a co-culture system, CT-treated $CD4^+$ T cells induced significantly less TNF-α and IL-12 p70 production by both autologous monocytes and monocyte-derived dendritic cells compared to LT-IIa- or LT-IIb-treated $CD4^+$ T cells. These findings thus demonstrate CT, LT-IIa, and LT-IIb differentially affect CD40-CD40L interactions between antigen-presenting cells and T cells, resulting in distinct cytokine profiles observed when type I and type II heat labile enterotoxins are used as mucosal adjuvants.

Figure 5A:
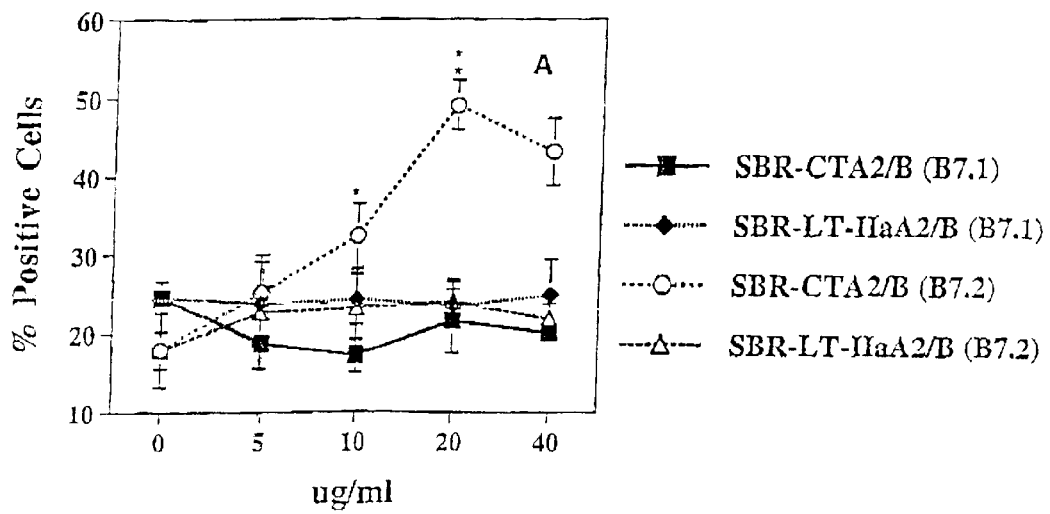
Figure 5B:
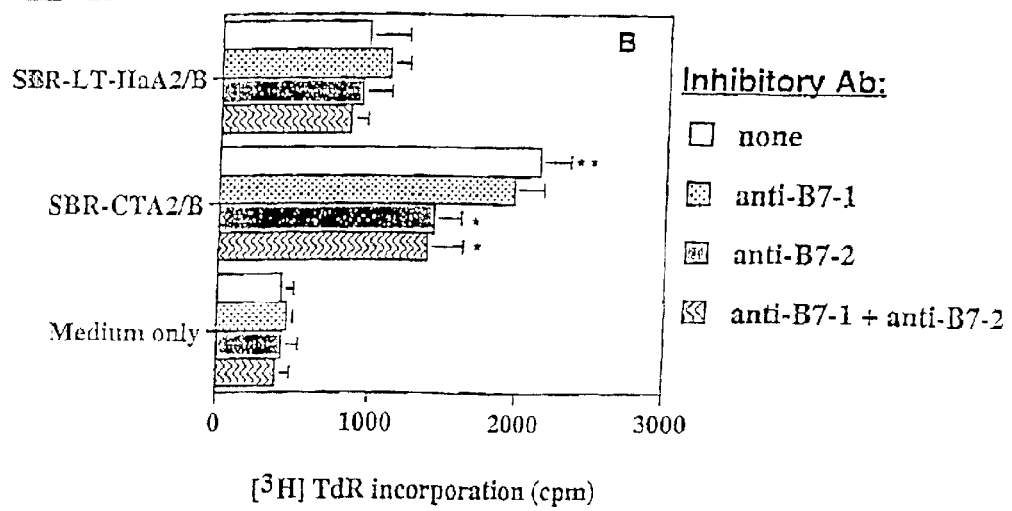

The present invention is directed to a method of inducing an immune response by administration of a recombinant immunogen expressed from a plasmid which comprises DNA sequence encoding a fusion protein of an antigen of interest fused in frame to the A2 subunit of a type II heat-labile enterotoxin. In one embodiment, the plasmid comprises salivary binding protein (SBR) from *Streptococcus mutans* surface protein (AgI/II) fused to the A2 subunit of *E. coli* heat-labile type IIa or type IIb toxin. The immunogen may be administered orally, intranasally, intrarectally, intravaginally, intramuscularly, or subcutaneously. In one aspect, the immune response results in the production of antibodies to the protein antigen sequence in saliva, intestinal secretions, respiratory secretions, genital secretions, tears, milk or blood. In another aspect, the immune response is development of antigen-specific T cells in the circulation and tissues, development of cytotoxic T cells or immunological tolerance to the protein antigen sequence.

The present invention is also directed to a method of inducing a B7-dependent immune response by administration of a recombinant immunogen expressed from a plasmid which comprises DNA sequence encoding a fusion protein of an antigen of interest fused in frame to the A2 subunit of cholera toxin. In one embodiment, the plasmid comprises salivary binding protein (SBR) from *Streptococcus mutans* surface protein (AgI/II) fused to the A2subunit of cholera toxin. The immunogen may be administered orally, intranasally, intrarectally, intravaginally, intramuscularly, or subcutaneously. The B7-dependent immune response is induction of B7-2 expression on B cells or antigen presenting cells, B7-2-mediated co-stimulation of T cell proliferation, enhanced IgG1 secretion or induction of Th2 immune responses. In one aspect, the immune response results in the production of antibodies to the protein antigen sequence in saliva, intestinal secretions, respiratory secretions, genital secretions, tears, milk or blood. In another aspect, the immune response is development of antigen-specific T cells in the circulation and tissues, development of cytotoxic T cells or immunological tolerance to the protein antigen sequence.

The present invention is also directed to methods of reducing CD40L expression on $CD4^+$ T cells, inhibiting TNF-α and IL-12 secretion from human PBMC or increasing cell-mediated immunity by administration of a recombinant immunogen expressed from a plasmid which comprises DNA sequence encoding a fusion protein of an antigen of interest fused in frame to the A2 subunit of cholera toxin or type II heat labile toxins.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1 shows the purification of recombinant mucosal immunogens. FIG. 1A shows SDS-PAGE of purified SBR-CTA2/B (lane 1) and SBR-LT-IIaA2/B (lane 2) dissociated into the SBR-A2 subunit (~60 kDa) and B subunit monomers (~12.5 kDa). FIG. 1B shows Western blot of recombinant SBR-CTA2/B (lane 1) and SBR-LT-IIaA2/B (lane 2) probed with polyclonal anti-SBR Abs, and of SBR-CTA2/B (lane 3) and SBR-LT-IIaA2/B (lane 4) using polyclonal Abs to CT or LT-IIa, respectively. The positions of the molecular mass markers (kilodaltons) are indicated. FIG. 1C shows titration of purified SBR-LT-IIaA2/B in a GD1-b-ELISA using polyclonal Abs to SBR and LT-IIa antigenic determinants. Each point represents the mean OD of triplicate values.

FIG. 2 shows IgA antibody production stimulated by recombinant mucosal immunogens. FIG. 2A shows salivary IgA responses to SBR after i.n. immunization of mice with SBR alone, SBR-CTA2/B, or SBR-LT-IIaA2/B. FIG. 2B shows vaginal IgA responses to SBR after i.n. immunization of mice with SBR alone, SBR-CTA2/B, or SBR-LT-IIaA2/B. Results are the arithmetic means ±SD of 8 mice per group. In A, * and **indicate statistically significant differences at $p<0.05$ and $p<0.01$, respectively, compared to SBR-LT-IIaA2/B.

FIG. 3 shows plasma antibody responses stimulated by recombinant mucosal immunogens. FIG. 3A shows plasma IgA antibody responses to SBR from mice immunized by the i.n. route with SBR alone, SBR-CTA2/B, or SBR-LT-IIaA2/B. FIG. 3B shows plasma IgG antibody responses to SBR from mice immunized by the i.n. route with SBR alone, SBR-CTA2/B, or SBR-LT-IIaA2/B. FIG. 3C shows plasma IgG subclass antibody responses (day 42) to SBR from mice immunized by the i.n. route with SBR alone, SBR-CTA2/B, or SBR-LT-IIaA2/B. Data represent the arithmetic means ±SD of 8 mice per group. *indicates statistically significant differences at $p<0.05$ compared to SBR-LT-IIaA2/B.

FIG. 4 shows antibody responses to the toxin components of the recombinant mucosal immunogens. FIG. 4A shows salivary IgA responses to CT or LT-IIa in mice immunized by the i.n. route with SBR-CTA2/B or SBR-LT-IIaA2/B, respectively. FIG. 4B shows vaginal IgA responses to CT or LT-IIa in mice immunized by the i.n. route with SBR-CTA2/B or SBR-LT-IIaA2/B, respectively. FIG. 4C shows plasma IgA responses to CT or LT-IIa in mice immunized by the i.n. route with SBR-CTA2/B or SBR-LT-IIaA2/B, respectively. FIG. 4D shows plasma IgG responses to CT or LT-IIa in mice immunized by the i.n. route with SBR-CTA2/B or SBR-LT-IIaA2/B, respectively. Data represent the arithmetic means ±SD of 8 mice per group. * and *** indicate statistical significance at $p<0.05$ and $p<0.001$, respectively.

FIG. 5 shows B7-dependent co-stimulation of T cells by the recombinant mucosal immunogens. FIG. 5A shows dose-response effect of SBR-CTA2/B and SBR-LT-IIaA2/B on B7-1 and B7-2 expression by $B220^+$ B cells. $B220^+$ B cells were incubated for 20 h with various concentrations of chimeric protein and then costained with anti-B7-1 and anti-B7-2. FIG. 5B shows proliferative responses of CD4+ T cells in the presence of anti-CD3 stimulation and B220+ cells that were unstimulated or treated with SBR-CTA2/B or SBR-LT-IIaA2/B in the absence or presence of inhibitory Abs to B7-1 or B7-2. * and ** indicate statistically significant differences at p<0.05, compared to no inhibitory Ab or SBR-LT-IIaA2/B, respectively. Results shown are expressed as the arithmetic mean ±SD of triplicate cultures.

FIG. 6 shows cytokine production by human PBMC cultured with 1 μg/ml of soluble anti-CD3 in the presence or absence of varying concentrations of CT, LT-IIa, or LT-IIb. After 48 to 72 h, cell-free supernatants were analyzed for cytokine concentrations: IL-4 (FIG. 6A), IL-10 (FIG. 6B), IL-2 (FIG. 6C), TNF-α (FIG. 6D) and IL-12 p70 (FIG. 6E). The data represents the mean ±SD of cultures derived from 4 donors. * indicates statistically significant differences at p<0.05 comparing CT- to LT-IIa- or LT-IIb-treated cultures.

Figure 7:
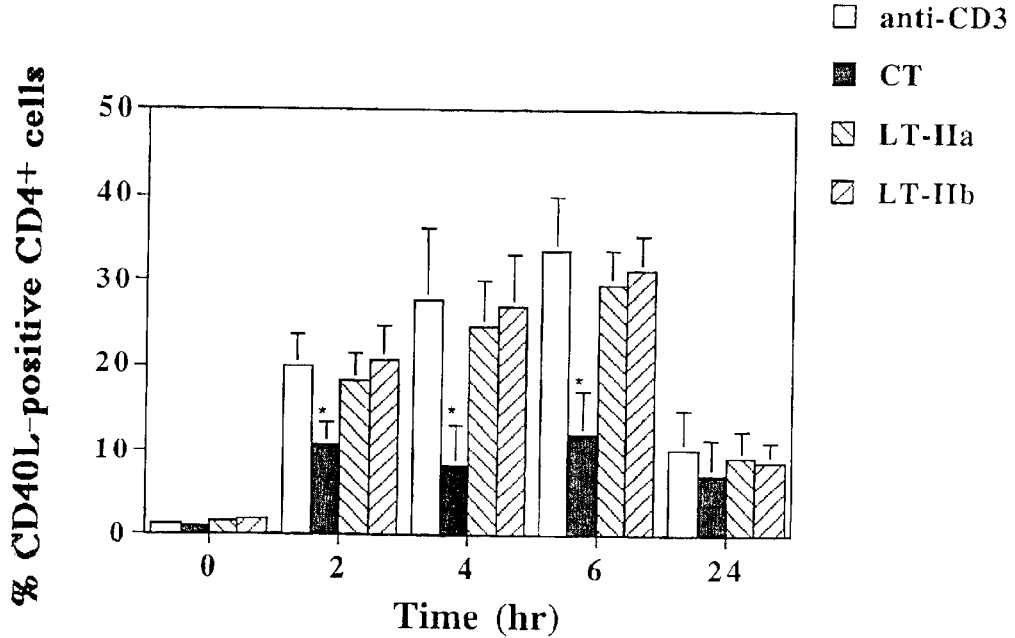
Figure 8A:
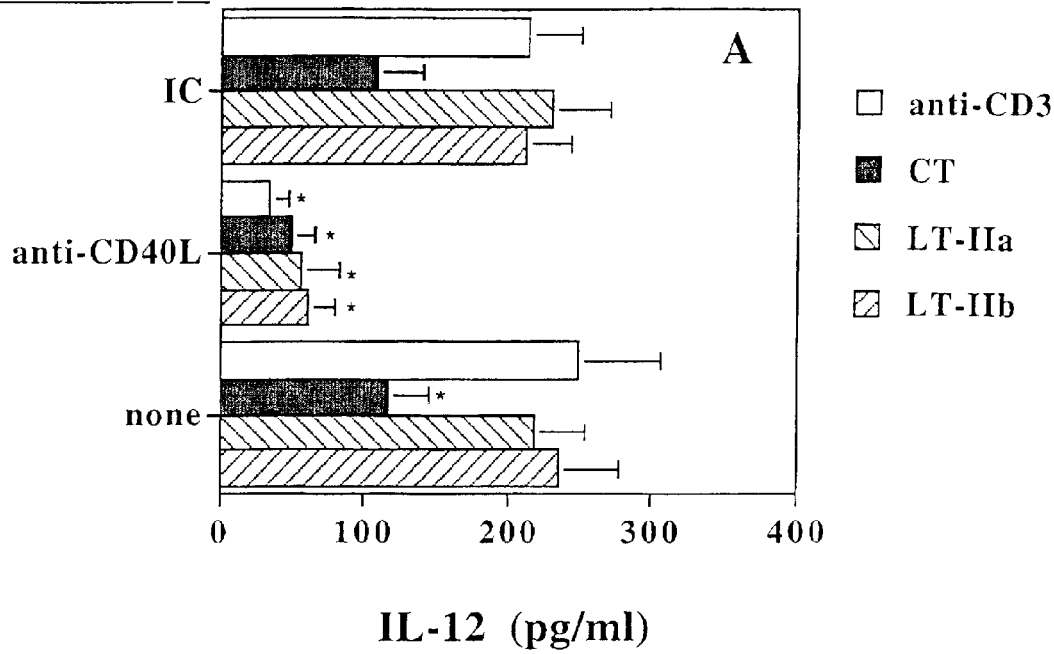
Figure 8B:
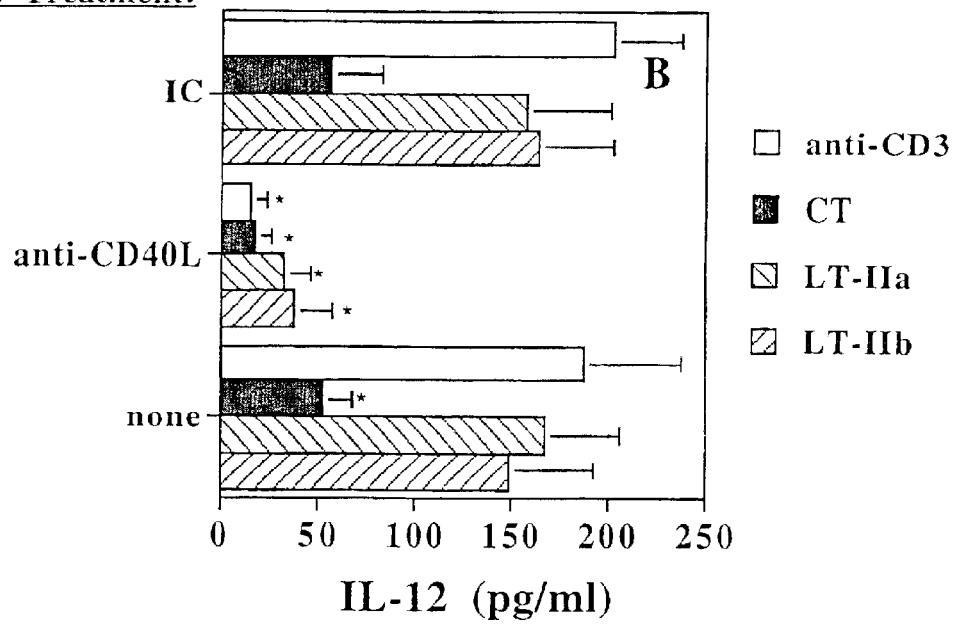
Figure 8C:
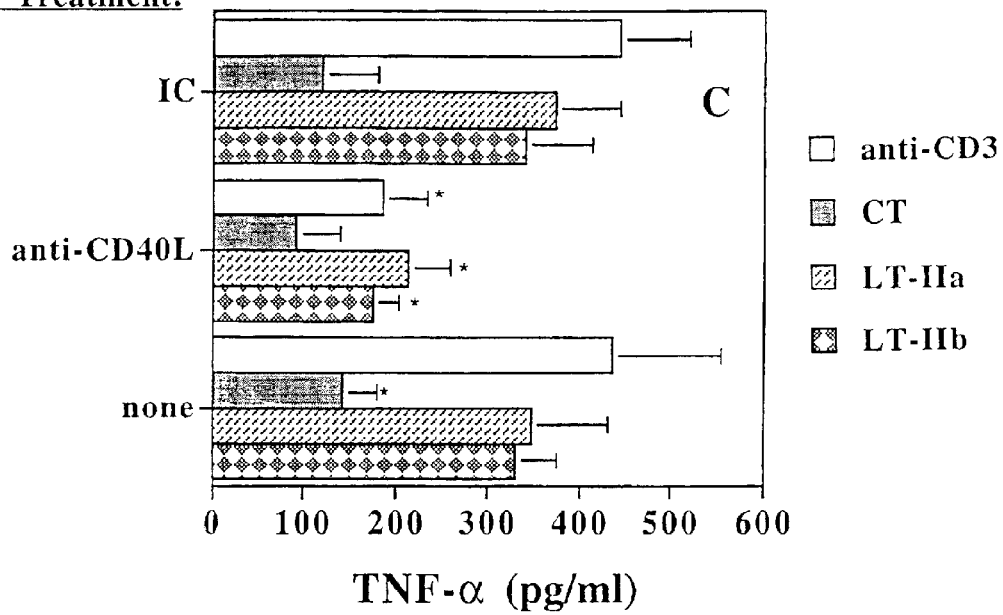
Figure 8D:
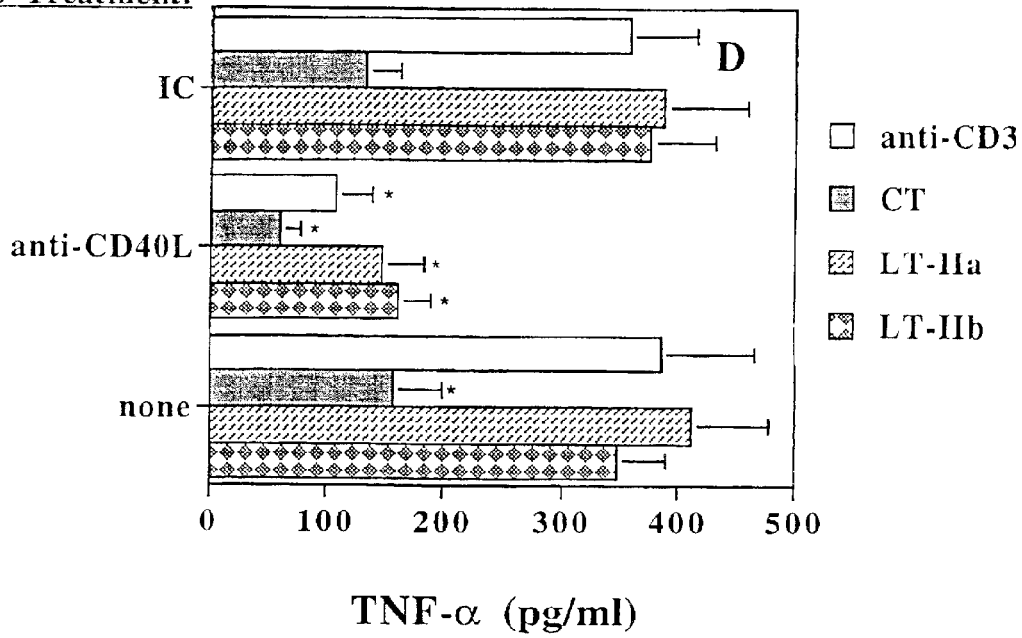

FIG. 7 shows expression of CD40L on CD4+ T cells. CD4+ T cells were cultured with or without 100 ng/ml of CT, LT-IIa, or LT-IIb in the presence of plate-bound anti-CD3 (5 μg/ml). CD40L expression on non-stimulated CD4+ T cells was less than 2.4% at all time points tested (data not shown). Data represent the mean ±SD of cultures derived from 4 donors. * indicates statistically significant differences at p<0.05 compared to anti-CD3 treated CD4+ T cells.

FIG. 8 shows production of IL-12 from monocytes (FIG. 8A) or monocyte-derived dendritic cells (FIG. 8B), or TNF-α production from monocytes (FIG. 8C) or monocyte-derived dendritic cells (FIG. 8D) co-cultured for 48 h with paraformaldehyde-fixed CD4+ T cells that were previously activated by plate-bound anti-CD3 in the presence or absence of CT, LT-IIa, or LT-IIb. Cultures were also performed in the presence of anti-CD40L Ab or an isotype matched control Ab (IC). Data represents the arithmetic mean ±SD of cultures derived from 4 donors. * indicates significant differences at p<0.05 compared to anti-CD3 treated CD4+ T cells.

DETAILED DESCRIPTION OF THE INVENTION

The following abbreviations may be used herein: CT: cholera toxin; CTA2/B: cholera toxin subunits A2/B; CTB: cholera toxin subunit B; i.n.: intranasal; LT-IIa: *E. coli* heat labile type IIa toxin; LT-IIaA2/B: heat labile type IIa toxin subunits A2/B; LT-IIb: *E. coli* heat labile type IIb toxin.

As used herein, the term "fusion protein" refers to a single contiguous protein produced by the expression of DNA sequences for one protein fused to DNA sequences encoding a different protein.

The ADP-ribosylating enterotoxins, cholera toxin (CT) and the *Escherichia coli* heat-labile type IIa toxin (LT-IIa), have been shown to enhance mucosal and systemic antibody (Ab) responses to co-administered antigens. In one aspect of the present invention, the abilities of the non-toxic A2/B subunits of these toxins to augment the immunogenicity of a genetically coupled protein antigen administered by a mucosal route were compared. Structurally similar chimeric proteins were generated by genetically replacing the enzymatically active A1 subunit of CT or LT-IIa with the saliva-binding region (SBR) from the streptococcal adhesin AgI/II. Intranasal immunization of BALB/c mice with either chimeric protein induced significantly higher plasma and mucosal anti-SBR IgA and IgG antibody (Ab) responses than SBR alone. Moreover, in comparison to SBR-LT-IIaA2/B, SBR-CTA2/B elicited significantly higher levels of plasma IgG (especially IgG1) and salivary IgA anti-SBR Ab responses. A functional mechanism for the observed differences in immunogenicity was due to differential effects of both chimeric proteins on the expression and co-stimulatory activity of B7-1 and B7-2 on murine splenic B cells. SBR-CTA2/B strongly up-regulated B7-2 but not B7-1 expression, whereas SBR-LT-IIaA2/B had only a minor effect on B7-1 and B7-2 expression. SBR-CTA2/B-treated B cells enhanced the proliferation of anti-CD3-stimulated CD4+ T cells, and this proliferation was reduced by treatment with anti-B7-2 but not with anti-B7-1 or an isotype-control Ab. Thus, SBR-CTA2/B and SBR-LT-IIaA2/B exhibit distinct patterns of antibody responses associated with differential effects on B7-2 expression and subsequent co-stimulatory effects on T cells.

In another aspect of the present invention, CT and the type II HLT were found to differentially affect cytokine production by anti-CD3 human peripheral blood mononuclear cells (PBMC), and the cellular mechanisms responsible were investigated. CT suppressed IL-2, TNF-α, and IL-12 production by PBMC cultures more than either LT-IIa or LT-IIb. CT, but not LT-IIa or LT-IIb, reduced the expression of CD4+ T cell surface activation markers (CD25 and CD69) and subsequent proliferative responses of anti-CD3 stimulated T cells. CT, but not LT-IIa or LT-IIb, significantly reduced the expression of CD40L on CD4+ T cells. In a co-culture system, CT-treated CD4+ T cells induced significantly less TNF-α and IL-12 p70 production by both autologous monocytes and monocyte-derived dendritic cells compared to LT-IIa- or LT-IIb-treated CD4+ T cells. These findings demonstrate that CT, LT-IIa, and LT-IIb differentially affect CD40-CD40L interactions between antigen-presenting cells and T cells and help explain the distinct cytokine profiles observed with type I and type II HLT when used as mucosal adjuvants.

In the present invention, there is provided a composition of matter comprising a plasmid for use as a mucosal immunogen. This recombinant plasmid expresses a chimeric protein which is a primary immunogen that induces differential immune responses. There are many potential uses in mucosal vaccine development. The basic method is amenable to almost any other protein antigen that can be cloned and inserted into the construct instead of SBR. Various applications of the present invention can be incorporated into commercial products, i.e., vaccines for the generation of immune responses that would afford protection against infections, or various modifications of the immune response. These are based on the use of chimeric proteins of A2/B subunits of enterotoxins that include protein segments from a variety of microorganisms intended for administration orally or intranasally, or possibly by other mucosal routes (e.g., rectally or intra-vaginally).

For example, one may prepare vaccines to generate immunity to the organisms responsible for dental caries, i.e., the mutans streptococci (*Streptococcus mutans* and *Streptococcus sobrinus*). This is based on the saliva-binding region of *S. mutans* AgI/II as described above. Furthermore, one may prepare vaccines against *Streptococcus pyogenes* (strep. throat and its sequelae including acute rheumatic fever and acute glomerulonephritis, scarlatina, streptococcal toxic shock, and other infections); prepare vaccines against *Streptococcus pneumoniae* (pneumococcal pneumonia, otitis media, meningitis) using sequences from pneumococcal surface proten A (PspA); vaccines against *Neisseria meningitidis* (meningococcal meningitis, otitis media) using neisserial surface protein A (NspA-men); vaccines against *Neis-* seria gonorrhoeae (gonorrhea) using neisserial surface protein A (NspA-gon); vaccines against *Streptococcus pneumoniae* (pneumococcal pneumonia, otitis media, meningitis) using other pneumococcal protein antigen; vaccines against *Streptococcus equi* ("strangles" in horses) using a *Streptococcus equi* surface protein; vaccines against influenza virus, *Helicobacter pylori* (gastric ulcer) and respiratory pathogens such as *Pseudomonas aeruginosa*; contraceptive vaccines using zona pellucida antigens; vaccine against respiratory syncytial virus; vaccines against mycoplasma infections; vaccines against *Staphylococcus aureus* protein A and generation of oral tolerance to auto-antigens (autoimmune conditions).

In yet another embodiment, the vaccine construction technology of the present invention can be used to generate immunity mediated by so-called cytotoxic T cells instead of antibodies. This methodology would have applications especially against viral infections.

The present invention is directed to a method of inducing an immune response by administration of a recombinant immunogen expressed from a plasmid which comprises, in operable linkage: a) an origin of replication; b) a promoter; c) DNA sequence encoding a fusion protein of an antigen of interest fused in frame to the A2 subunit of a type II heat-labile enterotoxin; and d) DNA sequence encoding subunit B of type II heat-labile enterotoxin for coexpression with the fusion protein of said antigen of interest to facilitate assembly of a chimeric protein. In one embodiment, the plasmid comprises salivary binding protein (SBR) from *Streptococcus mutans* surface protein (AgI/II) fused to the A2 subunit of *E. coli* heat-labile type IIa or type IIb toxin. One such preferred plasmid is designated pVAR9. The immunogen may be administered orally, intranasally, intrarectally, intravaginally, intramuscularly, or subcutaneously. In one aspect, the immune response results in the production of antibodies to the protein antigen sequence in saliva, intestinal secretions, respiratory secretions, genital secretions, tears, milk or blood. In another aspect, the immune response is the development of antigen-specific T cells in the circulation and tissues, the development of cytotoxic T cells or immunological tolerance to the protein antigen sequence.

The present invention is also directed to a method of inducing a B7-dependent immune response by administration of a recombinant immunogen expressed from a plasmid which comprises, in operable linkage: a) an origin of replication; b) a promoter; c) DNA sequence encoding a fusion protein of an antigen of interest fused in frame to the A2 subunit of cholera toxin; and d) DNA sequence encoding subunit B of cholera toxin for coexpression with the fusion protein of said antigen of interest to facilitate assembly of a chimeric protein. In one embodiment, the plasmid comprises salivary binding protein (SBR) from *Streptococcus mutans* surface protein (AgI/II) fused to the A2 subunit of cholera toxin. The immunogen may be administered orally, intranasally, intrarectally, intravaginally, intramuscularly, or subcutaneously. The B7-dependent immune response is the induction of B7-2 expression on B cells or antigen presenting cells, B7-2-mediated co-stimulation of T cell proliferation, enhanced IgG1 secretion or induction of Th2 immune responses. In one aspect, the immune response results in the production of antibodies to the protein antigen sequence in saliva, intestinal secretions, respiratory secretions, genital secretions, tears, milk or blood. In another aspect, the immune response is the development of antigen-specific T cells in the circulation and tissues, the development of cytotoxic T cells or immunological tolerance to the protein antigen sequence.

The present invention is further directed to methods of reducing CD40L expression on CD4$^+$ T cells, inhibiting TNF-α and IL-12 secretion in an individual or increasing Th1 response and cell-mediated immunity by administration of a recombinant immunogen expressed from a plasmid which comprises DNA sequence encoding a fusion protein of an antigen of interest fused in frame to the A2 subunit of cholera toxin or type II heat labile toxins. In general, the TNF-α or IL-12 is secreted from human PBMC, monocytes or monocyte-derived dendritic cells.

The following examples are given for the purpose of illustrating various embodiments of the invention and are not meant to limit the present invention in any fashion.

EXAMPLE 1

Plasmid Construct

The recombinant plasmid encoding the SBR-LT-IIa A2/B hybrid protein was constructed in two steps. The first step involved engineering an intermediate plasmid designated pSBR/KS+. The plasmid pSBR-CTA2/B (24) was digested with XbaI and XhoI to release a 1.2 kb fragment containing the SBR gene, a PelB leader sequence and a ribosomal-binding site. The 1.2 kb fragment, and all other fragments used in engineering the chimera, were isolated using agarose gel electrophoresis and a Gene Clean Kit (Bio101, Inc., Vista, Calif.), ligated into pBluescriptKS+ (Stratagene, La Jolla, Calif.) which had also been digested with XbaI and XhoI, and transformed into *E. coli* DH5αF' tet cells (Life Technologies, Bethesda, Md.) using osmotic shock.

In the second step, the polymerase chain reaction was used to amplify a fragment encoding the LT-IIa A2 domain and the B polypeptide from pTDC200, a plasmid which contained the genes encoding the type II HLT LT-IIa holotoxin (26, 27). The oligonucleotide primers Blue-619 (5'-GTAAAACGACGGCCAGTGAG-3') (SEQ ID No. 1) and Xho-I (5' GTAACCTCGAGGCCTGGAGAG-3') (SEQ ID No. 2) and a Perkin Elmer DNA Thermal Cycler Model 480 were used to amplify a 1025 bp fragment from pTDC200 (PCR conditions: denaturation at 92° C. for 30 sec, annealing at 52° C. for 60 sec, extension at 72° C. for 60 sec, 30 cycles). The amplified fragment was digested with SmaI which cleaved at a site located 3' to the terminus of the B polypeptide gene and with XhoI which was incorporated into the fragment using PCR primer Xho-I. This fragment was ligated into pSBR/KS+ that had been sequentially digested with KpnI, blunt-ended using Klenow, and digested with XhoI. Sites and oligonucleotides were chosen such that ligation of the fragments would place the SBR gene and the LT-IIa A2 sequences in the same reading frame. After transformation of the ligation mix into *E. coli* DH5αF' tet, a clone containing a plasmid encoding the SBR-LT-IIa A2/B chimera was isolated and verified by genetic sequencing. This plasmid was designated pVAR9. Since the chimeric gene was oriented into the vector such that expression depended upon the T7 promoter, pVAR9 was subsequently transformed into *E. coli* BL21 (DE3) which encodes an isopropyl-β-D-thiogalactoside (IPTG)-inducible T7 polymerase from a lysogenized prophage. A modified GD1b-ganglioside ELISA (27) and anti-SBR antiserum were used to demonstrate that the plasmid not only expressed the SBR-LT-IIaA2 and LT-IIa B polypeptides, but that the polypeptides assembled into the expected chimeric holotoxin and retained ganglioside binding activity (24).

EXAMPLE 2

Purification of Recombinant Proteins

Growth of *E. coli* and purification of recombinant SBR-CTA2/B were performed as previously described (24). To isolate SBR-LT-IIaA2/B, the *E. coli* strain expressing plasmid pVar9 was grown at 37° C. with vigorous shaking (225 rpm) in Luria-Bertani broth supplemented with ampicillin (150 µg/ml) and tetracycline (10 µg/ml). Target gene expression was induced at mid-log phase (OD ~0.4) by the addition of IPTG to 1 mM. Growth was terminated 12 to 16 hr after induction and cells were harvested by centrifugation. The bacterial pellet was re-suspended to $\frac{1}{10}$ the original culture volume in ice-cold 100 mM Tris-HCl, pH 8.0, containing 20% sucrose, 5 mM EDTA, and 0.5 mg/ml lysozyme to release the periplasm contents. After 30 min incubation at 4° C., the supernatant was harvested by centrifugation and subjected to 50% ammonium sulfate saturation. The subsequent precipitate was obtained by centrifugation and resuspended in 10 mM Tris-HCl, pH 8.0, containing 0.3 M NaCl. In order to separate properly assembled SBR-LT-IIaA2/B from unassembled SBR-A2 and B subunits, the dissolved precipitate was subjected to gel-filtration using a Sephacryl-100 (Pharmacia). Eluted fractions possessing anti-SBR reactivity in a GD1b-ELISA were then pooled and loaded onto an anion-exchange Mono Q column (Pharmacia). The fractions containing purified SBR-LT-IIaA2/B were determined by SDS-PAGE, Western blot and a GD1b-ELISA (27). Recombinant proteins were analyzed for endotoxin content by means of a Quantitative Chromagenic Limulus Amebocyte Lysate assay kit (Bio Whittaker, inc., Walkersville, Md.) using an *E. coli* K235 lipopolysaccharide standard. The endotoxin content for either recombinant protein was less than 0.5 ng of LPS per µg of purified chimeric protein.

EXAMPLE 3
Animals and Immunizations

Female BALB/c mice, 8 to 12 weeks of age, were immunized by the i.n. route. Groups of 6–8 mice were immunized four times at 7 day intervals (i.e., 0, 7, 14, and on day 21) with PBS, 50 µg SBR-CTA2/B, 50 µg SBR-LT-IIaA2/B, or an equimolar amount (20 µg) of SBR alone. The vaccines were administered in a standardized volume of 20 µl, applied slowly to both external nares of non-anaesthetized mice. All animal experiments were approved by the Institutional Animal Care and Use Committee at the University of Alabama at Birmingham.

EXAMPLE 4
Collection of Mucosal Secretions and Plasma

Samples of plasma, saliva and vaginal washes were collected from individual mice 1 day before the first immunization (day 0), and on days 8, 18, 28, 42 and 70. Saliva was collected with a micropipetter after stimulation of salivary flow by injecting each mouse intraperitoneally (i.p.) with 5 µg of carbachol (Sigma Chemical Company, St. Louis, Mo.) in 0.1 ml PBS. Plasma samples were obtained following centrifugation of blood collected from the tail vein using a calibrated heparinized capillary tube. Vaginal washes were collected by flushing the vaginal vault two times with 75 µl of sterile phosphate-buffered saline (PBS). Mucosal secretions and plasma samples were stored at −70° and −20° C., respectively, until assayed for antibody activity.

EXAMPLE 5
Antibody Analysis

The levels of isotype-specific antibodies in saliva, plasma and vaginal washes were assayed by ELISA. Polystyrene microtiter plates (96-well; Nunc, Roskilde, Denmark) were coated overnight at 4° C. with 5 µg/ml of SBR, 2 µg/ml of GD1b, or 1 µg/ml of GM1 (Matreya, Pleasant Gap, Pa.). GM1- and GD1b-treated plates were washed and incubated with CT (1 µg/ml) or LT-IIa (2 µg/ml), respectively, for 30 min at 37° C. Total Ig isotype concentrations were determined by coating plates with goat anti-mouse Ig isotype-specific antibodies (Southern Biotechnology Associates, Birmingham, Al.). Serial two-fold dilutions of plasma or secretion samples were added in duplicate and plates were incubated overnight at 4° C. Plates were then washed with PBS containing 0.1% Tween (PBS-Tw) and incubated at room temperature with the appropriate peroxidase-conjugated goat anti-mouse Ig isotype-specific reagent (Southern Biotechnology). Plates were washed and developed with o-phenylenediamine and hydrogen peroxide. Color reaction was stopped after 15 min and optical density measured at 490 nm. The levels of antibodies and of total Ig in samples were calculated by interpolation on calibration curves generated by using a mouse Ig reference serum (ICN Biomedicals, Aurora, Ohio). In order to compensate for variations arising from salivary flow rate and dilutions of secretions, mucosal IgA responses are reported as the level of specific antibody IgA/total IgA.

EXAMPLE 6
Purification of B220$^+$ B and CD4$^+$ T Cells

Splenic CD4$^+$ T cells were purified by use of magnetized polystyrene beads (Dynabeads) coated with a rat mAb specific for the CD4 (L3T4) membrane Ag (Dynal A.S., Oslo, Norway). Briefly, a single cell suspension of splenocytes was incubated at 4° C. for 20 min in the presence of mouse CD4 Dynabeads. CD4$^+$ T cells were then positively selected with the aid of a Dynal magnetic particle concentrator. CD4$^+$ T cells were then washed three times in PBS containing 1% fetal calf serum (FCS) and 2 mM EDTA. Isolated CD4$^+$ T cells were then detached from L3T4 Dynabeads using a DETACHaBEAD Mouse CD4 Ag (Dynal A.S., Oslo, Norway). Cells were then washed three times and resuspended in complete medium [RPMI 1640; (Cellgro Mediatech, Washington D.C.) containing 10% FCS, 40 µm 2-mercaptoethanol, 1% L-glutamine, 10 mM HEPES, 10 U/ml penicillin, 100 µg/ml streptomycin, and 50 µg/ml gentamycin] before use. This procedure routinely resulted in >99% pure CD4$^+$ T cells as shown by flow cytometry.

B220$^+$ B cells were isolated from the CD4$^+$ depleted splenocyte population by use of a depletion column using CD43 MicroBeads (Miltenyi Biotec, Sunnyvale, Calif.). CD43 MicroBeads were incubated with the cell suspension for 15 min at 6° C. in PBS containing 0.5% BSA and 2 mM EDTA. The cell suspension was then washed by adding a 20-fold excess of PBS containing 0.5% BSA and 2 mM EDTA. After centrifugation, cells were resuspended in 1 ml PBS-0.5% BSA and added to the magnetic depletion column. CD43 B cells were eluted with 15 ml of PBS containing 0.5% BSA and 2 mM EDTA. Cells were then washed twice and resuspended in complete medium before use. This procedure routinely yielded >pure 99% B220$^+$ cells as shown by flow cytometry.

EXAMPLE 7
Cell Staining and Proliferation Assay

To examine the effects of SBR, SBR-CTA2/B, SBR-LT-IIaA2/B, rLT-IIa B and rCTB on co-stimulatory molecule upregulation by B cells, B220$^+$ B cells (1×10$^6$ cells/ml) were incubated with various concentrations of recombinant proteins. In order to assess the effects of ganglioside binding, SBR-CTA2/B or SBR-LT-IIaA2/B, were first blocked by incubating with a 20:1 molar ratio of GM1 or GD1b, respectively, (Matreya, Pleasant Gap, Pa.) for 1 h at 37° C. and then added to B220$^+$ cell cultures. Following a 20 h incubation, B cells were incubated for 15 min in PBS containing 0.1% sodium azide and 3% FCS and washed extensively. B cells were then co-stained with fluorescein isothiocyanate (FITC)-conjugated anti-B7-2 or phycoerythrin (PE)-conjugated anti-B7-1 (Pharmingen). Fluorochrome-labelled cells were analyzed by flow cytometry using a FACStar flow cytometer (Becton Dickinson, Mountain View, Calif.).

To assess the co-stimulatory function of B7-1 and B7-2 upregulation, B cells were treated with SBR-CTA2/B, SBR-LT-IIaA2/B, or media alone for 20 h, washed in ice-cold PBS, and fixed in 0.5% paraformaldehyde. CD4$^+$ T cells ($2\times10^6$ cells/ml) were cultured in complete medium containing 0.5% paraformaldehyde fixed B cells ($1\times10^6$ cells/ml) in the presence of 100 ng/ml of anti-CD3 Ab for 5 days. Approximately 18 h before harvesting, the cells were pulsed with 0.5 $\mu$Ci of [$^3$H]-thymidine, and [$^3$H]-thymidine uptake was determined by using a liquid scintillation counter.

EXAMPLE 8
Characterization of the Expressed Chimeric Protein SBR-LT-IIaA2/B

Periplasmic fractions of *E. coli* expressing SBR-LT-IIaA2/B were purified by gel filtration and anion-exchange chromatography. Eluted fractions were monitored by GD1b-ELISA and SDS-PAGE. As shown by SDS-PAGE and Western blot, SBR-LT-IIaA2/B was purified to homogeneity and contained both antigenic determinants, SBR and LT-IIa (FIGS. 1A and B). Furthermore, purified SBR-LT-IIaA2/B was shown to bind GD1b-coated plates and contained both SBR and LT-IIa epitopes, indicating successful assembly of an intact chimeric protein that possessed ganglioside binding (FIG. 1C). These results, along with the nature of the genetic construction of the chimeric protein indicate that SBR-LT-IIaA2/B is structurally similar to the SBR-CTA2/B chimeric protein (24) in possessing equimolar ratios of SBR and A2/B$_5$ subunits.

EXAMPLE 9
Antibody Responses to SBR in Mucosal Secretions

Figure 2A:
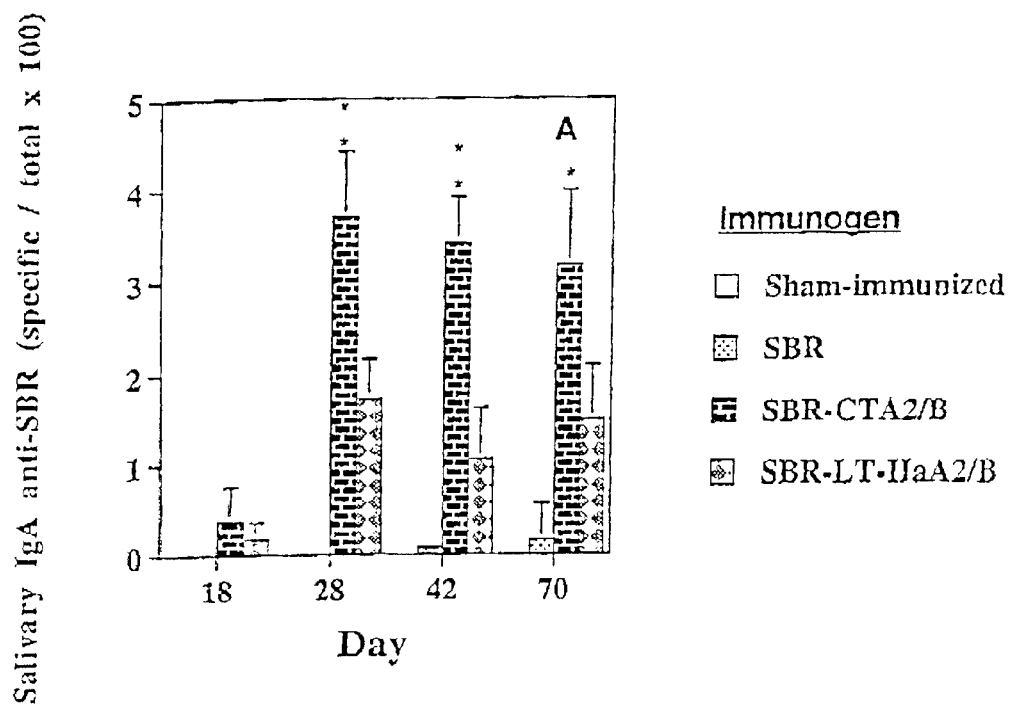
Figure 2B:
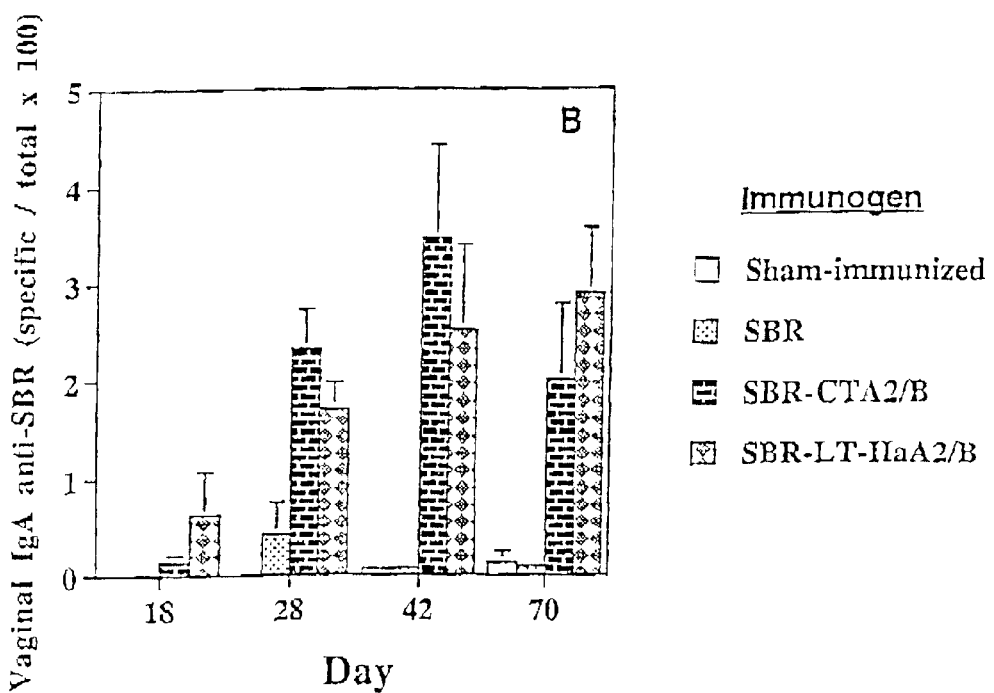

In order to compare the mucosal immunogenicity of SBR, SBR-CTA2/B and SBR-LT-IIaA2/B, groups of mice were immunized by the i.n. route with equimolar amounts of each immunogen and saliva and vaginal wash samples were analyzed for IgA anti-SBR activity. Both chimeric proteins induced SBR-specific IgA in saliva that persisted at greater than 1% of total salivary IgA through day 70 (FIG. 2A). SBR-CTA2/B and SBR-LT-IIaA2/B induced maximal levels of salivary IgA anti-SBR Abs on day 28, which reached almost 4% and 2% of total salivary IgA, respectively (FIG. 2A). On days 28 through 70, mice immunized with SBR-CTA2/B had significantly higher levels (P<0.05) of SBR-specific IgA in the saliva than mice immunized with SBR-LT-IIaA2/B (FIG. 2A). Vaginal IgA anti-SBR Ab responses were detected on day 18 in mice immunized with SBR-CTA2/B or SBR-LT-IIaA2/B and persisted at high levels through day 70 (FIG. 2B). Peak vaginal anti-SBR IgA (3.6%) levels in SBR-CTA2/B mice occurred on day 42, while peak responses in mice immunized with SBR-LT-IIaA2/B (~3%) occurred on day 70. Mice immunized with SBR alone had low to non-detectable levels of SBR-specific Abs in saliva (FIG. 2A) and vaginal wash (FIG. 2B). These results suggest that SBR-CTA2/B was more effective at inducing salivary IgA Abs to SBR than SBR-LT-IIaA2/B. However, this effect was not observed in vaginal wash samples.

EXAMPLE 10
Plasma Antibody Responses to SBR

Figure 3A:
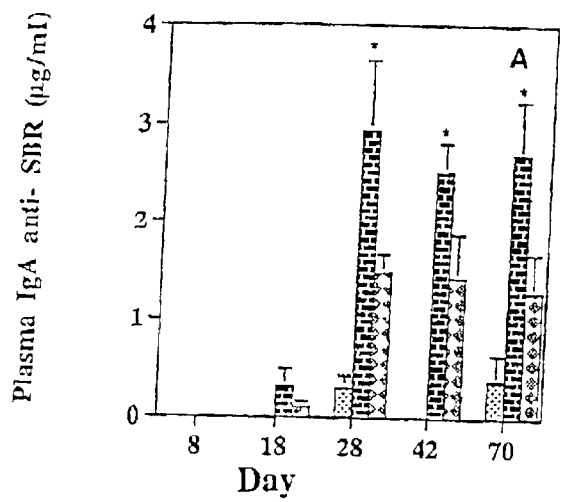
Figure 3B:
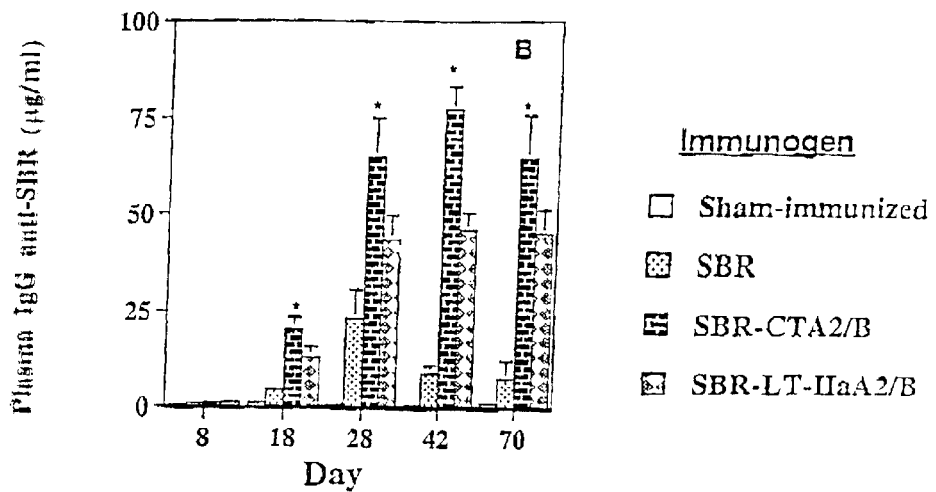
Figure 3C:
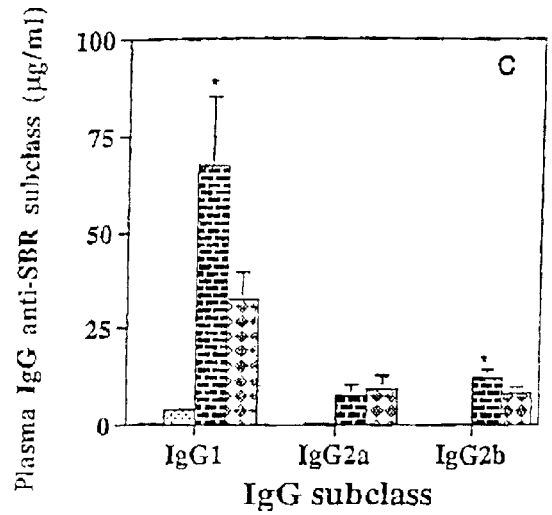

Mice immunized by the i.n. route with SBR-CTA2/B or SBR-LT-IIaA2/B had significantly (P<0.05) higher (3- to 10-fold) levels of plasma IgA anti-SBR Abs compared to mice immunized with SBR alone (FIG. 3A). On days 28 through day 70, SBR-CTA2/B immunized mice had significantly (P<0.05) higher levels of SBR-specific plasma IgA compared to mice immunized with SBR-LT-IIaA2/B (FIG. 3A). Plasma IgG anti-SBR levels were also significantly elevated in mice immunized with SBR-CTA2/B or SBR-LT-IIaA2/B compared to SBR alone (FIG. 3B). Furthermore, on days 18 to 70, plasma IgG anti-SBR Abs were significantly (P<0.05) higher in mice immunized with SBR-CTA2/B than in mice receiving the SBR-LT-IIaA2/B chimera (FIG. 3B). Analysis of the IgG subclasses revealed that the major SBR-specific subclass was IgG1, followed by lower levels of IgG2a and IgG2b (FIG. 3C). SBR-specific IgG1 Ab in SBR-CTA2/B immunized mice was significantly elevated compared to SBR or SBR-LT-IIaA2/B immunized mice (FIG. 3C). Furthermore, the ratios of SBR-specific IgG1:IgG2a were markedly different between groups. Mice immunized with SBR-CTA2/B had an IgG1:IgG2a ratio of 10:1, whereas those immunized with SBR-LT-IIaA2/B had an IgG1:IgG2a ratio of 4:1 (FIG. 3C). Thus, it appears that the greater IgG Ab response induced by SBR-CTA2/B is largely due to a selective increase in IgG1 Abs.

Table 1 shows a comparison of serum IgG and IgA antibody responses in mice immunized with phosphate-buffered saline (control), SBR (20 $\mu$g), SBR-CTA2/B chimeric protein (50 $\mu$g), SBR-LT(IIa)A2/B chimeric protein (50 $\mu$g) or SBR-LT(IIb)A2/B chimeric protein (50 $\mu$g). Groups of 6 mice each were immunized intranasally 3 times at 10-day intervals (i.e. days 1, 11, and 21), and serum samples were collected 7 days after the third dose (i.e. day 28). Serum antibodies were assayed by ELISA against whole AgI/II, and are expressed as $\mu$g/ml.

TABLE 1

Serum Antibody induced by SBR, SBR-CTA2/B, SBR-LT-IIaA2/B, or SBR-LT-IIbA2/B

| Ab Class | Control | SBR | SBR-CTA2/B | SBR-LT(IIa)A2/B | SBR-LT(IIb)A2/B |
|---|---|---|---|---|---|
| IgG Mean ± SD | 0 | 6.88 ± 5.72 | 30.73 ± 24.38 | 24.32 ± 13.69 | 63.69 ± 44.80 |
| IgG Geo.Mean x/÷SD | 0 | 5.27 x/÷2.23 | 17.42 x/÷4.68 | 20.58 x/÷1.98 | 50.49 x/÷2.24 |
| IgA Mean ± SD | 0 | 0.24 ± 0.59 | 0.68 ± 1.09 | 0.38 ± 0.24 | 1.61 ± 1.17 |
| IgA Geo.Mean x/÷SD | 0 | 0.16 x/÷2.98 | 0.27 x/÷4.72 | 0.34 x/÷2.00 | 1.08 x/÷3.50 |

EXAMPLE 11
Antibody Responses to CT and LT-IIa

Figure 4A:
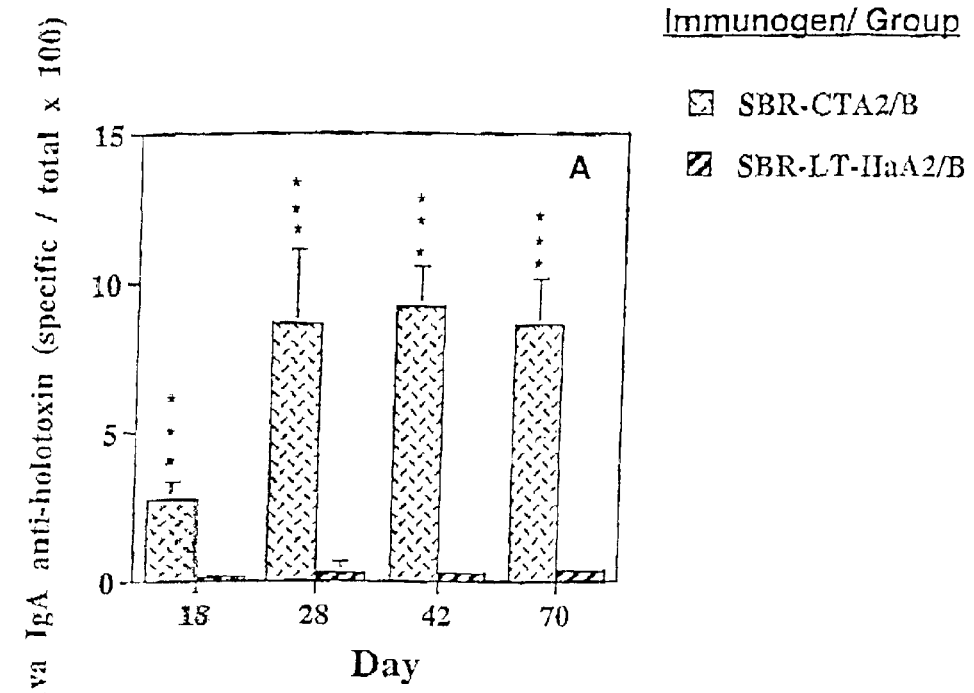
Figure 4B:
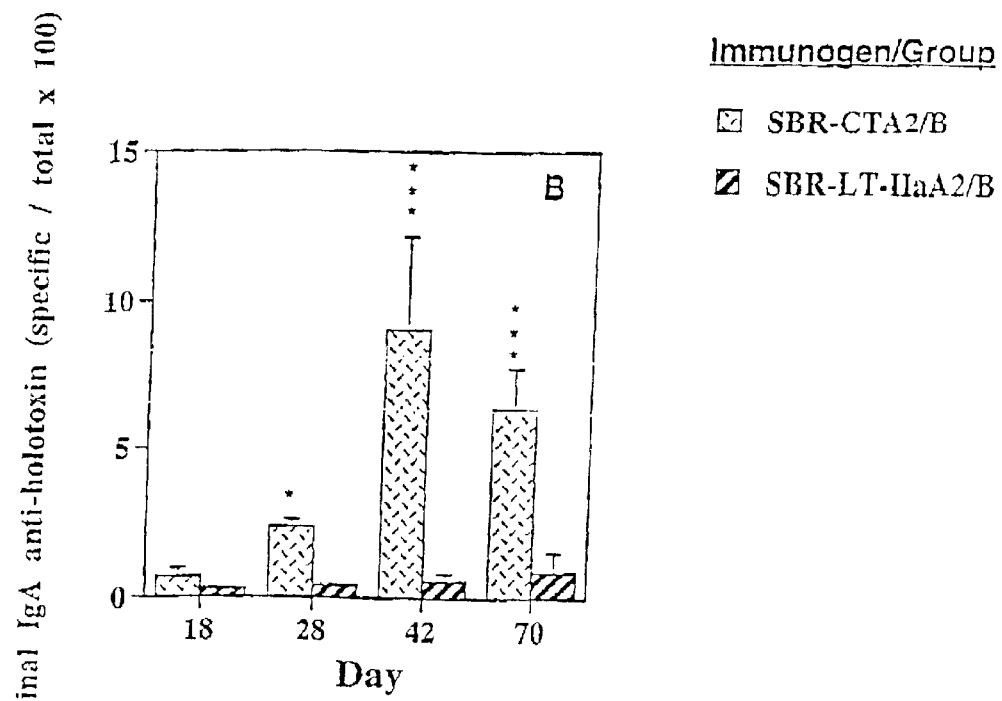
Figure 4C:
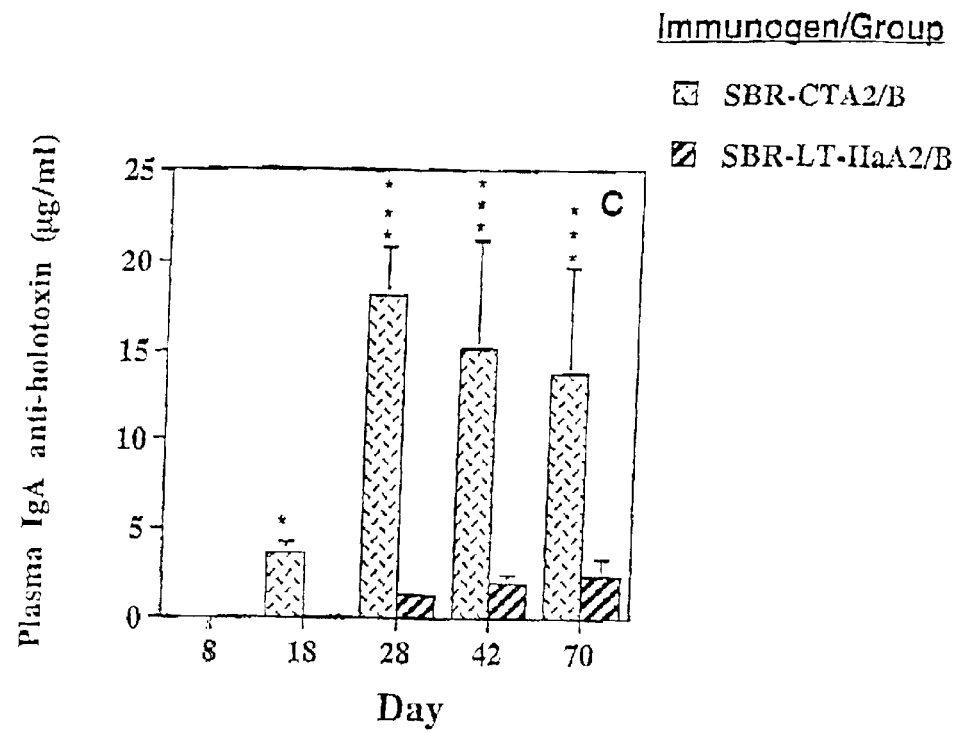
Figure 4D:
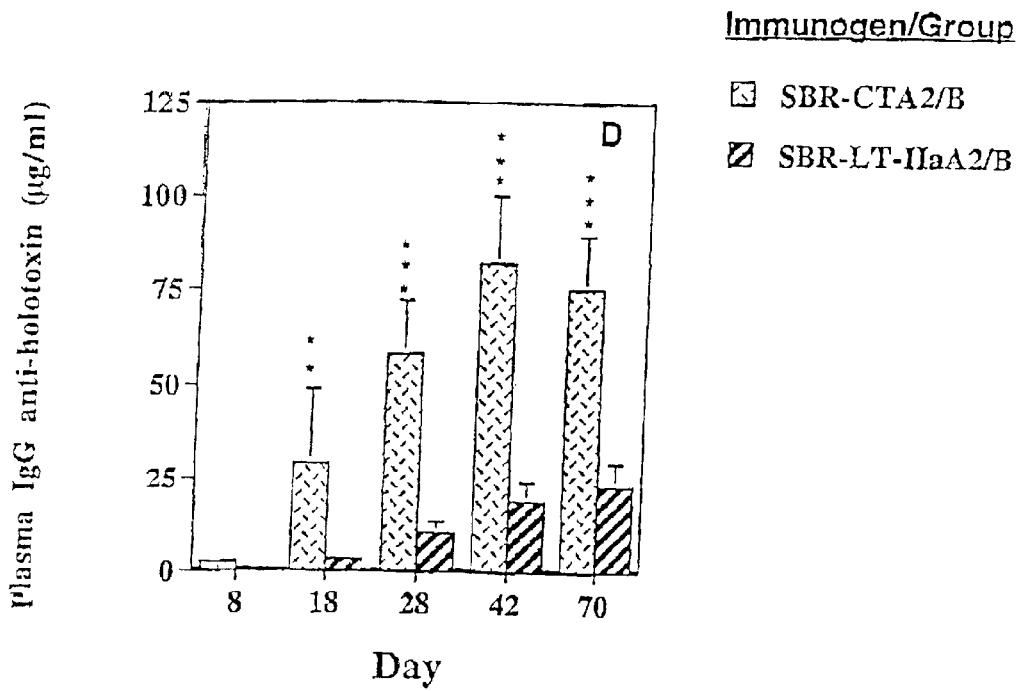

The immunogenicity of the CTA2/B and LT-IIaA2/B components of the two chimeras was also analyzed by employing a ganglioside-dependent ELISA (28). Optimal concentrations of GM1, GD1b, CT and LT-IIa for coating the assay plates were first determined by titration curves generated with various concentrations of the ganglioside, CT, and LT-IIa. SBR-CTA2/B induced significantly higher (P<0.05 to P<0.001) salivary IgA and vaginal IgA anti-CT Ab compared to the anti-LT-IIa Ab responses induced in mice immunized with SBR-LT-IIaA2/B (FIGS. 4A, 4B). Plasma IgA and IgG Ab responses to LT-IIa were likewise lower than the anti-CT responses (FIGS. 4C, 4D). These data demonstrate that the CTA2/B subunits of CT were consistently more immunogenic than the LT-IIaA2/B subunits of LT-IIa in the respective chimeras.

EXAMPLE 12
Expression of B7-1 and B7-2 on B Cells

Several studies have demonstrated the importance of B7 molecules on antigen-presenting cells in providing co-stimulatory function for T cell activation (29, 30). Furthermore, it has been shown that the adjuvanticity of CT is strongly dependent upon the upregulation of B7-2 expression (31). However, it is not known if the immunogenicity of Ags genetically coupled to the B subunit depends on B7 upregulation. Therefore, the issues of whether SBR-CTA2/B and SBR-LT-IIaA2/B could upregulate B7-1 or B7-2 expression on splenic B cells, and if the differences in immune responses to these immunogens might be related to differential effects on B7 expression were examined. Incubation of SBR-CTA2/B with splenic B cells from naive mice resulted in a significant upregulation of B7-2 expression, which was greater than 5-fold higher than that induced by SBR-LT-IIaA2/B (Table 2). In contrast, SBR-CTA2/B had no effect on B7-1 expression on B220+ cells. SBR or rCTB alone caused no change in B7-1 expression and only a modest increase in B7-2 (Table I). rLT-IIa B alone induced a similar increase in B7-1 expression as seen with SBR-LT-IIaA2/B. but did not affect B7-2 expression (Table 2). The upregulation of B7-2 by SBR-CTA2/B was dose-dependent, reaching a maximum at 20 µg/ml (FIG. 5A). In contrast, SBR-LT-IIaA2/B had only a minor effect on B7-1 and B7-2 expression at all concentrations tested (FIG. 5A). To demonstrate that the upregulation of B7 expression by the chimeric proteins was dependent upon ganglioside binding, SBR-CTA2/B and SBR-LT-IIaA2/B were incubated with GM1 or GD1b, respectively, before addition to B cell cultures. Pretreatment of either chimera with its receptor significantly reduced B7 expression by B cells to levels accountable for by the effect of SBR alone (Table 2). These results demonstrate that SBR-CTA2/B and SBR-LT-IIaA2/B differ in their ability to enhance B7-1 and B7-2 expression, and suggest that the upregulation of B7 depends on recognition of the chimeras by their respective ganglioside receptors.

To determine if the observed increases in B7 expression on B cells promoted a functional co-stimulatory activity, CD4+ T cell proliferative responses were assessed. Splenic CD4+ T cells were stimulated with a sub-optimal concentration of anti-CD3 in the presence of B cells that had previously been incubated with SBR-CTA2/B or SBR-LT-IIaA2/B (or medium alone) and then fixed with paraformaldehyde. CD4+ T cells cocultured with untreated B cells (medium only) displayed a low level of stimulation by anti-CD3 (FIG. 5B). SBR-LT-IIaA2/B-treated B cells did not significantly enhance T cell proliferation under anti-CD3 stimulation compared to untreated B cells (FIG. 5B). In contrast, B cells incubated with SBR-CTA2/B induced significantly ($p<0.05$) higher T cell proliferative responses compared to both the SBR-LT-IIaA2/B-treated and control groups (FIG. 5B). To determine if the increased CD4+ T cell proliferation in response to B cells was dependent on B7 upregulation, mAbs to B7-1 or B7-2, or isotype control Abs were added to the cultures. The mAb anti-B7-1, anti-B7-2 or both had little effect on the B cell co-stimulatory activity induced by SBR-LT-IIaA2/B (FIG. 5B). The addition of mAb anti-B7-1 had no significant effect on T cell proliferation induced by SBR-CTA2/B-treated B cells. In contrast, the addition of mAb anti-B7-2 significantly ($p<0.05$) diminished the T cell proliferative response induced by SBR-CTA2/B-treated B cells (FIG. 5B). Isotype control Abs did not have any effect on proliferative responses (Data not shown). These data suggest that the enhanced co-stimulation of T cells by SBR-CTA2/B-treated B cells was associated with B7-2, but not B7-1 upregulation.

TABLE 2

Expression of B7-1 and B7-2 on splenic B220+ cells treated with SBR-CTA2/B, SBR-LT-IIaA2/B, SBR, rCTB, or rLT-IIa B[a]

| Stimulant | % increase positive cells: | |
|---|---|---|
| | B7-1 | B7-2 |
| SBR-CTA2/B | <1[b] | 37.03 ± 7.67 |
| SBR-LT-IIaA2/B | 4.78 ± 2.16 | 7.18 ± 2.87 |
| SBR | <1 | 4.67 ± 2.93 |
| rCTB | <1 | 8.49 ± 2.12 |
| rLT-IIaB | 5.87 ± 3.15 | <1 |
| SBR-CTA2/B (GM1-treated) | <1 | 5.49 ± 2.33 |
| SBR-LT-IIaA2/B (GD1b-treated) | <1 | 4.66 ± 3.19 |

[a]B220+ splenic cells (1 × 10$^6$/ml) were incubated with 20 µg/ml of chimeric protein or equimolar concentrations of SBR, rCTB, or rLT-IIaB for 20 h. Cells were washed and costained with PE-conjugated anti-B7-1 and FITC-conjugated anti-B7-2.
[b]Values are the percent increase in the expression of B7 molecules are shown as the difference between experimental and control (untreated) from three separate experiments (mean ± SD).

Discussion

The above examples demonstrate the construction and expression of a recombinant chimeric protein in which the ADP-ribosylating A1-subunit of LT-IIa was genetically replaced with SBR from the streptococcal adhesin AgI/II. This chimera, designated SBR-LT-IIaA2/B, was shown to act as a mucosal immunogen which induced significantly higher anti-SBR Ab responses in both plasma and mucosal secretions compared to an equivalent dose of SBR alone. However, the immunogenicity of a previously constructed chimeric protein based on CT (24), designated SBR-CTA2/B, was significantly greater than that observed with SBR-LT-IIaA2/B. The greater immunogenicity of SBR-CTA2/B was revealed in higher salivary and serum IgA Abs to the SBR component, and in a selective enhancement of IgG1 subclass Abs. These results suggest that the CT-based chimera had a greater capacity to induce responses governed by type 2 T helper cells (Th2). A similar bias was found in our previous studies on the comparative adjuvant properties of the intact holotoxins, CT and the type II HLE (21). The lower Th2 inducing capacity of SBR-LT-IIaA2/B may conversely permit greater expression of Th1 activity, as also indicated by the previous study (21). A further possible advantage of chimeric mucosal immunogens based on LT-IIa rather than CT is that they induce substantially lower Ab responses to the HLE component of the immunogen. This feature may permit the repeated administration of an LT-IIaA2/B-based chimeric protein without the loss of immunogenicity due to pre-existing Abs against the HLE. A mechanism contributing to the differences in the immunogenicity induced by the two chimeras appears to be associated with marked differences in B7 upregulation and subsequent costimulatory effects on CD4+ T cells.

The adjuvant properties of CT have been associated with the ADP-ribosyltransferase activity of the A1-subunit (4, 32). Moreover, elevated intracellular cAMP induced by CT, or the use or cAMP analogs, has been shown to enhance the expression of B7-2 on B cells and macrophages (31, 33). In contrast, data presented here clearly show that SBR-CTA2/B, which lacks the ADP-ribosylating A1-subunit, significantly enhanced B7-2 expression on B cells, which in turn induced a functional costimulatory signal for CD4$^+$ T cells. A recent study by others using a non-toxic mutant of cholera toxin has also demonstrated that B7 enhancement by CT was not dependent upon ADP-ribosyltransferase activity (9). Taken together, these data show that ADP-ribosylation or subsequent enhancement of cAMP are not required for B7 upregulation on B cells.

Earlier studies addressing the effects of B7-1 and B7-2 on T helper cells suggested that these two B7 molecules do not confer equivalent costimulatory signals. Unlike B7-1, B7-2 preferentially stimulates IL-4 production from human T cells and may be initially involved in establishing the Th2-phenotype (29, 34). Moreover, it has been reported that Th1 and Th2 cells differ in their requirements for CD28 ligation. The initial activation of Th2 cells is highly dependent upon B7-CD28 interactions, whereas Th1 cells initially appear to be less dependent on CD28 ligation, but require B7-CD28 interactions for their maintenance (30, 35). A study assessing the adjuvant properties of CT demonstrated that blocking B7-2-CD28 interactions resulted in a down regulation of Ag-specific IgG1 but not IgG2a in vivo, and that the adjuvant properties of CT were the result of preferentially upregulating B7-2 (31). The present results with SBR-CTA2/B are in agreement with these observations. SBR-CTA2/B significantly enhanced B7-2 expression which, in turn, provided a costimulatory signal via B7-2 to CD4$^+$ T cells. Moreover, analysis of the IgG subclasses revealed that the enhanced IgG Abs observed in mice immunized with SBR-CTA2/B was due to the selective enhancement of IgG1 Abs which, compared to responses in mice immunized with SBR-LT-IIaA2/B, exhibited more than a two-fold increase in the ratio of SBR-specific IgG1:IgG2a, indicative of a Th2-dominated immune response (36, 37). Thus, the selective enhancement of B7-2 may play a critical role in the IgG1-dominated Ab subclass response observed in SBR-CTA2/B immunized mice.

The chimeric protein SBR-LT-IIaA2/B induced significantly lower plasma and mucosal Ab responses, as well as costimulatory B7 expression, than SBR-CTA2/B. However, SBR-LT-IIaA2/B did exhibit enhanced mucosal immunogenicity compared to an equimolar amount of SBR alone. One proposed mechanism responsible for the immunoenhancing effect of chimeric proteins based on HLE B subunits is their targeting of cell surface gangliosides resulting in enhanced immunogen uptake. It has recently been shown that the conjugation of rCTB to the surface of liposomes greatly enhanced their adjuvant properties compared to liposomes containing rCTB in the encapsulated aqueous phase (38). Subsequent studies using both surface-linked and encapsulated rCTB demonstrated enhanced uptake of rCTB-coated liposomes by murine Peyer's patches. Therefore, compared to SBR alone, the ability of SBR-LT-IIaA2/B to target cell-surface gangliosides could result in the enhanced uptake and increased delivery of Ag to immunocompetent cells.

Previous studies addressing the immunogenicity of CT and LT-I in various mice strains have demonstrated that the immunogenicity of type I heat-labile toxins is governed by the H-2 haplotype (2, 39). Therefore, the observed differences in the anti-CT and anti-LT-IIa Ab responses may be due to the particular immune response haplotype of the mouse strain (BALB/c) used in this study. However, the adjuvanticity of CT is not restricted by the H-2 haplotype (40). A previous study demonstrated that, while the immunogenicity of CT was significantly greater than that observed with either LT-IIa or LT-IIb, there was no correlation between the immunogenic and adjuvant properties of CT, LT-IIa, and LT-IIb in BALB/c mice (21). Thus, results concerning the immunoenhancing effect of both chimeras on the Ab response to SBR are not likely to be dependent upon the H-2 haplotype.

The upregulation of B7 molecules by both SBR-CTA2/B and SBR-LT-IIaA2/B was dependent upon recognition of their respective ganglioside receptors. Due to their genetic construction, these two chimeras are structurally similar and differ only at the amino acid level in their $A2/B_5$ components, which confer different ganglioside-binding properties. Thus, the lower immunoenhancing effect of SBR-LT-IIaA2/B may be the result of its selective binding to non-GM1 receptors or possibly the result of its lower affinity for GM1 compared to SBR-CTA2/B (20). Previous studies addressing receptor-mediated immunomodulation by the B subunit of the type I HLE LT-I showed that targeting its high- affinity receptor, GM1, was largely responsible for its immunogenic and adjuvant properties (8, 10). Despite the ability of LT-I B to bind non-GM1 receptors, GM1 appears to be its dominant receptor (20). Moreover, a recent study has demonstrated that membrane lipid rafts enriched in GM1, which are believed to play an important role in signal transduction and membrane trafficking, were targeted to the MHC class II peptide-loading compartment after B cell receptor crosslinking (41, 42). Therefore, the ability to target GM1 may also increase Ag-delivery and subsequent MHC class II presentation by B cells.

Activation of $CD4^+$ T cells requires, in addition to recognition by the T cell receptor of antigenic peptide in the context of MHC class II, co-stimulation of CD28 by B7 molecules on the APC (29, 30). B cells normally serve as APC in the secondary immune response, when adequate numbers of specific antibody-expressing cells are available from the clonal expansion occurring in the primary immune response. Previous studies addressing the effects of the HLE and their B subunits on B lymphocyte functional activation (9, 10, 31), as well as data presented here, demonstrate that B cells can become activated prior to interaction with T cells and subsequently express high levels of B7 costimulatory molecules and thereby serve as APC. The recruitment of activated B cells expressing these phenotypic markers has been shown to be important for the activation of naive T cells (43). Furthermore, experiments addressing germinal center formation by Ag-specific B lymphocytes during the initial immune response suggest that as few as two or three activated B cells are required for the induction of productive T:B cell interaction (44). Thus, the low frequency of Ag-specific B cells during a primary immune response is not likely be a limiting factor for the activation of naive T cells, when HLE-coupled immunogens are used. Thus, even in a primary immune response, it is possible that chimeric immunogens based on HLE exert their immunoenhancing effect, at least in part, by recruiting B cells as APC.

EXAMPLE 13

The following examples demonstrate distinct cytokine regulation by cholera toxin and the type II heat-labile toxins involving differential regulation of CD40L on $CD4^+$ T cells.

After mucosal administration, both type I and type II heat-labile enterotoxin (HLT) have been shown to enhance T helper (Th) cytokine production from both systemic and mucosal lymphoid compartments. However, there appear to be marked differences in both the Th1 and Th2 cytokine profiles induced by these enterotoxins (45,46). Several studies have shown that CT induces a predominant Th2 response with increased production of IL-4, IL-5, and IL-10, and subsequent elevated levels of antigen-specific IgG1 Ab (45–48). With the aid of IL-4$^{-/-}$ knockout mice, it was further demonstrated that the adjuvanticity of CT is highly dependent upon Th2-associated cytokines (49). Compared to CT, the type II HLT, LT-IIa and LT-IIb, have been shown to induce a more balanced Ag-specific Th1 and Th2 cytokine profile and IgG subclass response (45). However, the mechanism responsible for these observed differences remains to be elucidated.

An important factor during the initial phase of an immune response that determines whether Th cells will develop into Th1 or Th2 effector cells depends upon the presence of IL-12 and IL-4, respectively. CD40 ligand (CD40L) or CD154, is a type II transmembrane protein that is transiently expressed on CD4$^+$ T cells, which recognizes CD40 on B cells, monocytes/macrophages, and dendritic cells (50). CD40-CD40L interactions have been demonstrated to be important for the induction of IL-12 from APC (51, 52). IL-12, which consists of a p40 and p35 chain linked via a disulfide bond, promotes the differentiation of naive CD4$^+$ T cells into Th1 effector cells while suppressing the development of Th2 type responses (53–55). Consistent with these findings, CD40L$^{-/-}$ mice have been shown to have defective Th1 responses while concomitantly exhibiting elevated IL-4 production compared to wild type mice (56). Thus, the regulation of CD40-CD40L interactions appears to play an important role in determining the function of Th cells.

Studies in the present example were focused on whether CT and the type II enterotoxins differentially affect CD40L expression on CD4$^+$ T cells and the subsequent CD40-CD40L-dependent IL-12 production from APC. It was found that CT, but not LT-IIa or LT-IIb, significantly inhibited T cell activation and the up-regulation of CD40L expression on CD4$^+$ T cells after anti-CD3 stimulation. Using a co-culture system, CT-, LT-IIa-, and LT-IIb-treated CD4$^+$ T cells differentially affected CD40-CD40L-dependent TNF-α and IL-12 production by both autologous monocytes and monocyte-derived dendritic cells.

LT-IIa and LT-IIb holotoxins were derived from an *E. coli* XL-1 Blue (Stratagene) strain transformed with plasmids pTDC200 or pTDC101, respectively (27). Growth and purification of LT-IIa and LT-IIb were done as previously described (45). CT was purchased from List Biological Laboratories. Human anti-CD3 and neutralizing human anti-CD40L Abs were obtained from Pharmingen (San Diego, Calif.). Recombinant human IL-4, IFN-γ, and GM-CSF were purchased from R & D Systems (Minneapolis, Minn.).

EXAMPLE 14

Isolation and Stimulation of Human PBMC, CD4$^+$ T cells, Monocytes, and Dendritic Cells Human PBMC were obtained from healthy donors and isolated from heparinized venous blood by isolating the buffy coat and eliminating RBC contamination by histopaque (SG-1.077) density gradients. After washing in PBS containing 1% fetal calf serum (FCS) and 2 mM EDTA, PBMC were re-suspended at a concentration of 2×10$^6$ cells/ml in complete culture medium RPMI 1640 (Cellgro Mediatech, Washington D.C.) containing 10% FCS, 1% L-glutamine, 10 mM HEPES, 10 U/ml penicillin, 100 μg/ml streptomycin, and 50 μg/ml gentamycin, and then stimulated with soluble anti-CD3 (1 μg/ml) in the presence or absence of the desired holotoxin (1 to 1000 ng/ml). Cell-free supernatants were collected after incubation for 48 to 72 h and stored at −20° C. until assayed for cytokine production.

CD4$^+$ T cells were purified from isolated human PBMC with the aid of a CD4$^+$ T cell indirect magnetic labeling kit containing monoclonal hapten-conjugated CD8, CD11b, CD16, CD19, CD36, and CD56 Abs (Miltenyi Biotec). As determined by flow cytometry, this procedure routinely yielded >95% CD4$^+$ T cells. CD4$^+$ T cells were pre-incubated with CT, LT-IIa, or LT-IIb (1 to 1000 ng/ml) for 1 h and then stimulated with plate-bound anti-CD3 (5 μg/ml). CD4$^+$ T cells were then stained for CD25, CD69, or CD40L expression using antibodies obtained from Pharmingen and analyzed by flow cytometry.

To determine the functional consequence of CD40L expression on CT-, LT-IIa-, or LT-IIb-treated CD4$^+$ T cells, after anti-CD-3 stimulation for 6 h, CD4$^+$ T cells were fixed with 1% paraformaldehyde, washed extensively in complete RPMI, and co-cultured at a concentration of 2×10$^6$ cells/ml with autologous monocytes or monocyte-derived dendritic cells (1×10$^6$ cells/ml) in the presence or absence of anti-CD40L or an isotype-matched control Ab.

Monocytes were isolated from PBMC by depletion of non-monocyte cells, which was performed with the aid of an indirect magnetic isolation kit using monoclonal hapten-conjugated CD3, CD7, CD19, CD45RA, CD56, and IgE Abs (Miltenyi Biotec). This procedure routinely resulted in >90% pure CD14$^+$ cells as shown by flow cytometry.

Dendritic cells were derived from monocytes purified by negative selection as described above. Briefly, monocytes were cultured for 7 days in the presence of 100 ng/ml of IL-4 and GM-CSF and non-adherent cells were harvested. The majority of the resulting cells (>80%) excluded trypan blue, >60% expressed CD1a, and exhibited characteristic dendrite formation.

EXAMPLE 15

Cytokine Analysis

Cell-free culture supernatants were assayed for cytokine concentration by ELISA by using reagents for human IL-2, IL-4, IL-10, IL-12, IFN-γ and TNF-α obtained from R & D systems. Briefly, flat-bottomed 96-well microtiter plates (Nunc) were coated with mouse monoclonal anti-IL-2, anti-IL-4, anti-IL-10, anti-IL-12, anti-IFN-γ, or anti-TNF-α at 1 μg/ml in PBS and incubated overnight at 4° C. Plates were washed with PBS-Tween (PBS-Tw) and blocked to limit non-specific binding with 10% FCS in PBS for 1 h at 37° C. After washing the plates, supernatants were serially diluted in 1% BSA in PBS and added to the wells. Standard curves were generated using serial dilutions of recombinant IL-2 (2000 pg/ml), IL-4 (2000 pg/ml), IL-10 (2000 pg/ml), IL-12 (2,000 pg/ml), IFN-γ (2000 pg/ml), or TNF-α (1000 pg/ml). Plates were incubated at 4° C. overnight followed by washing with PBS-Tw. Appropriate secondary antibodies, consisting of either biotin- or peroxidase-labeled goat antibodies, were added to plates. In assays using biotinylated antibodies, a 1/1000 dilution of horseradish peroxidase-conjugated streptavidin containing 1% BSA in PBS-Tw was added to the appropriate wells and plates were incubated at room temperature for 2 h. The reaction was developed for 20 min with o-phenylenediamine-H$_2$O$_2$ substrate and stopped with 1 M H$_2$SO$_4$. The color reaction was measured at 490 nm.

EXAMPLE 16

Flow Cytometry

PBMCs or CD4$^+$ T cells were cultured at a concentration of 2×10$^6$ cells/ml in complete culture medium and stimulated with soluble (1 μg/ml) or plate-bound (5 μg/ml) anti-CD3 in the presence or absence of CT, LT-IIa, LT-IIb (1 to 1000 ng/ml). Cells were harvested, centrifuged, and re-suspended in FACS buffer (PBS containing 3% FCS and 0.1% NaN$_3$ for 15 min and then centrifuged. Cells were then re-suspended in FACS buffer and stained with CD25-FITC, CD69-PE, CD1a-PE, C40L-PE, and co-stained with CD4-APC (Pharmingen). After a 30 min incubation at 4° C., cells were washed in FACS buffer, and re-suspended in 1% paraformaldehyde. Fluorochrome-labelled cells were analyzed by flow cytometry using a FACStar flow cytometer (Becton Dickinson, Mountain View, Calif.).

EXAMPLE 17

Figure 6A:
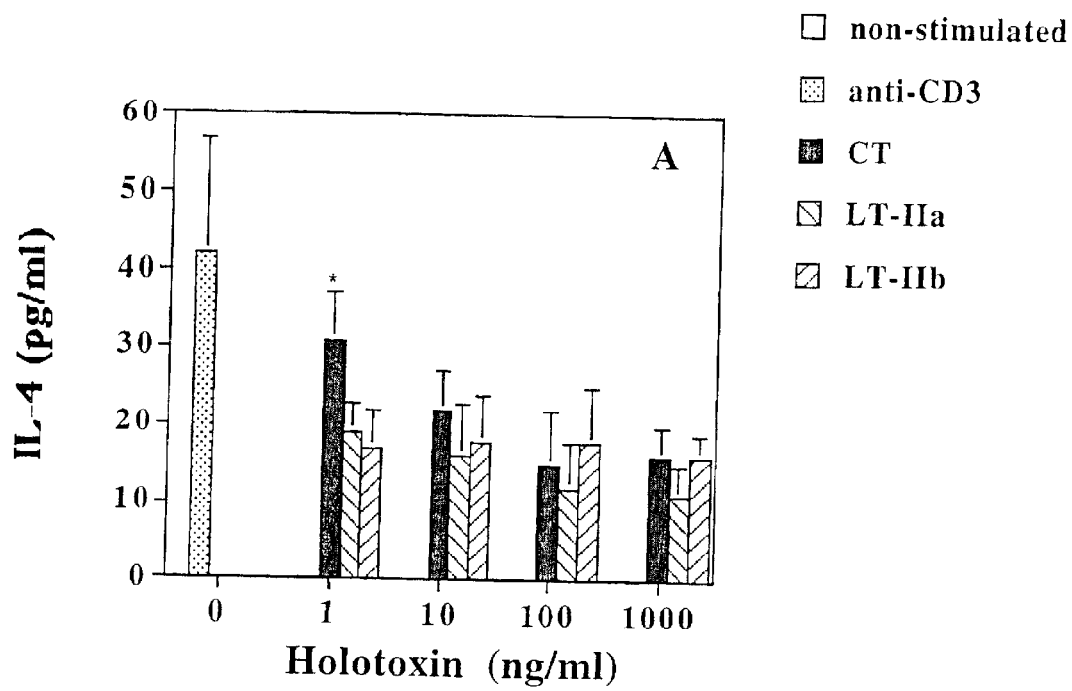
Figure 6B:
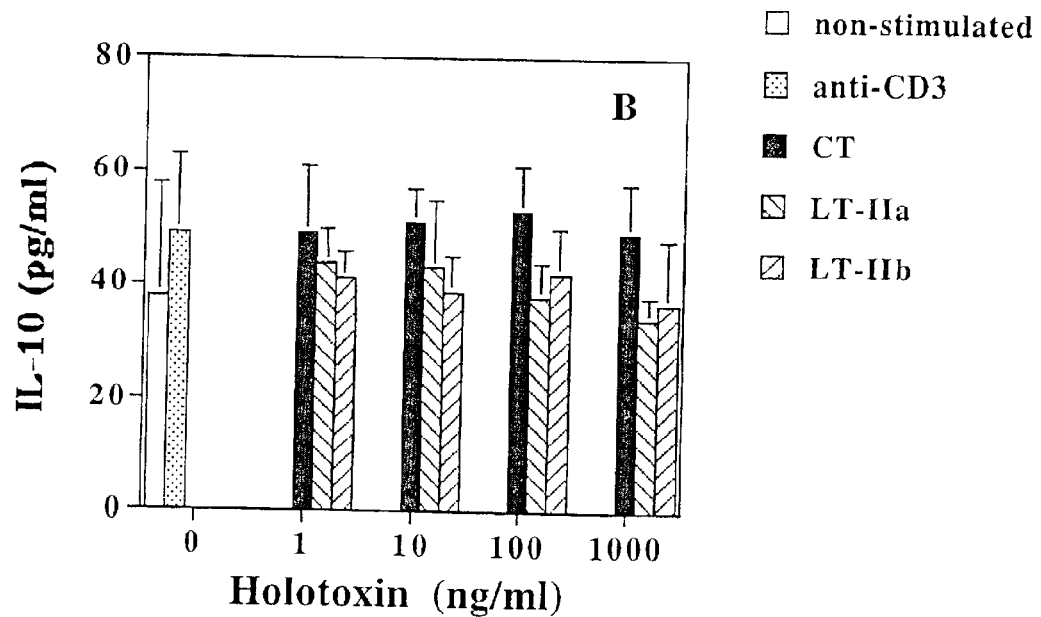
Figure 6C:
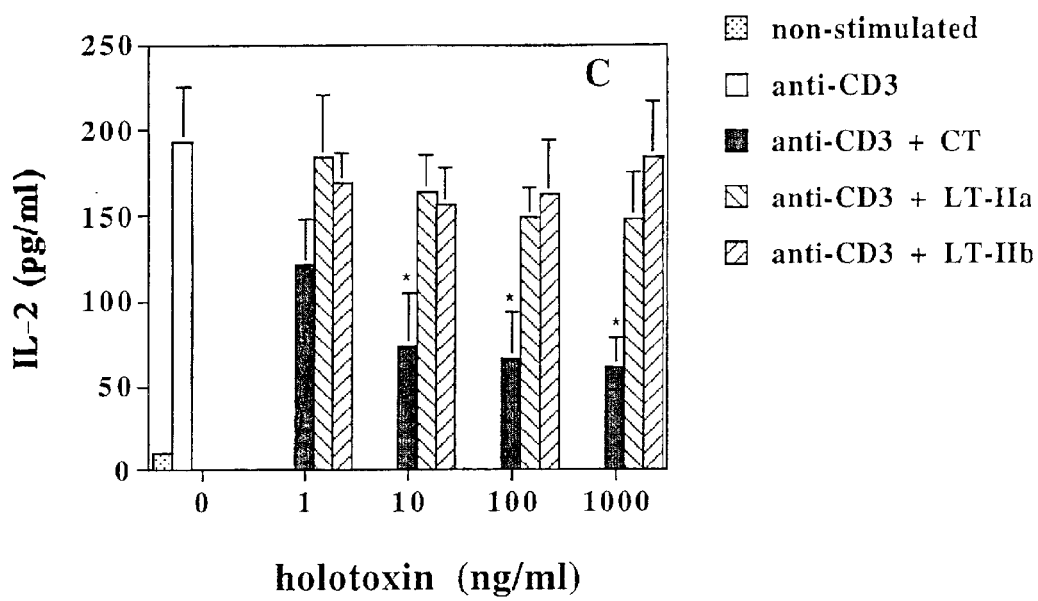
Figure 6D:
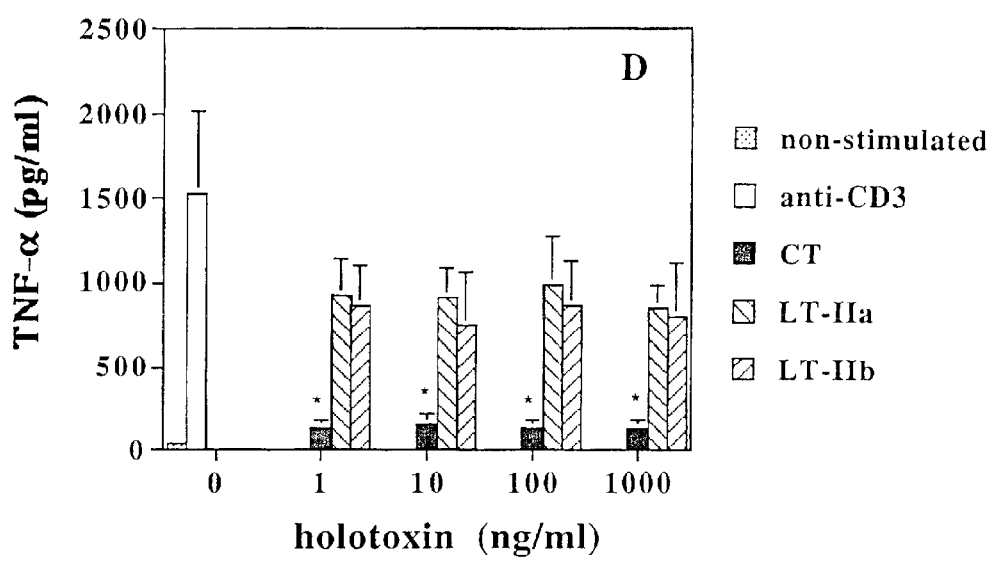
Figure 6E:
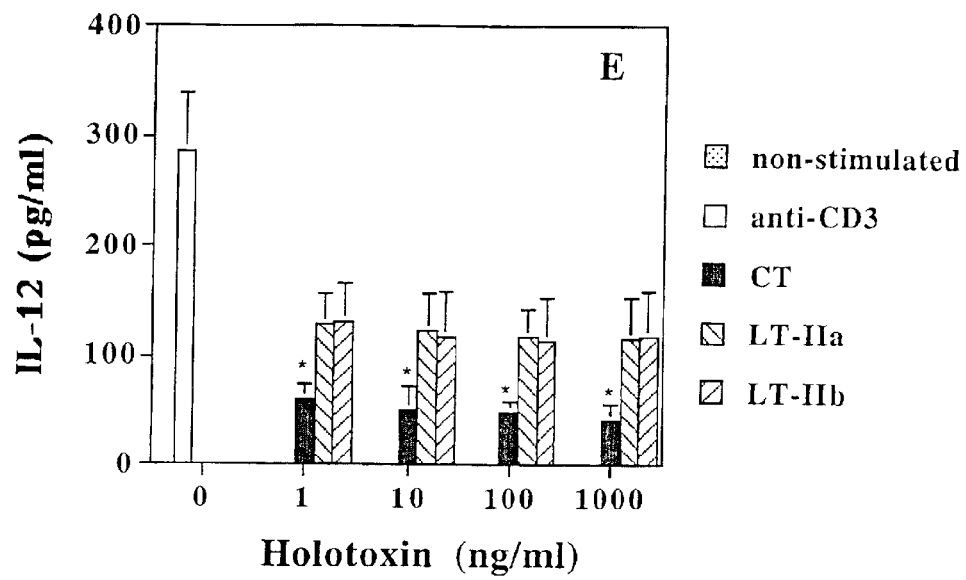

CT, LT-IIa, and LT-IIb Differentialy Affect Cytokine Production from Anti-CD3 Stimulated PBMC It was previously found that CT and the type II HLT exhibit different effects on the production of Th1 and Th2 cytokines from mouse lymphocytes (45). In order to determine if similar effects occurred in human PBMC, cytokine profiles induced in CT-, LT-IIa-, or LT-IIb-treated, soluble anti-CD3 mAb-activated human PBMC were analyzed. Cell-free supernatants were collected 48 to 72 h after stimulation and analyzed for cytokine production by ELISA. No significant differences in the level of IL-4 or IL-10 were observed between CT-, LT-IIa, or LT-IIb treated PBMC cultures (FIGS. 6A, 6B). In contrast, CT-treated PBMC exhibited a pronounced reduction in IL-2, TNF-α, and IL-12 p70 production compared to PBMC treated with LT-IIa or LT-IIb (FIGS. 6C–E). These data agree with previous findings on the effects of type I and type II HLT on the immune response in mice and demonstrate that CT and the type II HLT differentially affect Th cytokine production from anti-CD3 treated human PBMC.

EXAMPLE 18

CT, LT-IIa, and LT-IIb Differentially Affect the Activation and Proliferation of Anti-CD3 Stimulated PBMC Experiments were then performed to determined whether CT and the type II HLT could be influencing cytokine production from APC by affecting T cell activation. PBMC were cultured with soluble anti-CD3 for 24 h in the presence or absence of holotoxin and then CD4$^+$ T cells were analyzed by flow cytometry for T cell activation markers. Anti-CD3 stimulation significantly increased CD25 and CD69 expression on CD4$^+$ T cells, compared to untreated controls (Table 3). However, when PBMC were stimulated with anti-CD3 in the presence of CT, a significantly lower mean level of both CD25 and CD69 expression was seen on CD4$^+$ T cells compared to controls, whereas LT-IIa and LT-IIb exhibited minimal inhibitory effects on the expression of CD25 and CD69 (Table 3). Similarly, CT inhibited the proliferation of anti-CD3-stimulated PBMC, while LT-IIa and LT-IIb had no significant effect on proliferation (Table 3). Thus, there are significant differences in the ability of CT, LT-IIa, and LT-IIb to suppress T cell activation and subsequent proliferation.

TABLE 3

Effects of CT, LT-IIa, and LT-IIb on T cell activation and proliferation

| Stimulant | Toxin (100 ng/ml) | Surface expression of: CD25[a] (% +ve) | CD69[a] (% +ve) | [$^3$H] thymidine incorporation[b] (cpm) |
|---|---|---|---|---|
| None | — | 3.48 ± 1.51 | 2.96 ± 2.68 | 421 ± 189 |
| anti-CD3 | — | 30.77 ± 5.94 | 26.55 ± 4.29 | 32747 ± 7459 |
| anti-CD3 | CT | *6.83 ± 3.22 | *8.47 ± 5.63 | *7992 ± 2359 |
| anti-CD3 | LT-IIa | 25.55 ± 6.02 | 21.49 ± 5.95 | 28956 ± 5625 |
| anti-CD3 | LT-IIb | 23.44 ± 5.63 | 21.88 ± 3.31 | 26331 ± 6523 |

[a]Cell surface expression of CD25 and CD69 were analyzed by FACS following a 24 h incubation.
[b][$^3$H]-thymidine was added during the last 18 h of a 72 h culture. Data represent the mean ± SD of cultures derived from 4 donors.
*indicates statistically significant differences at p < 0.05 compared to anti-CD3 treated PBMCs.

Effects of CT, LT-IIa, and LT-IIb on CD40L Expression

Whether the observed differences in the effects of CT and the type II HLT on activation and cytokine production by anti-CD3 stimulated PBMC were related to an alteration in the up-regulation of CD40L was examined next. If so, this could influence IL-12 production by APC through interaction with CD40. Since CD40L is expressed predominantly on CD4$^+$ T cells, PBMC were treated with or without CT, LT-IIa, or LT-IIb, stimulated with anti-CD3 for 2 to 24 h, and then the CD4$^+$ T cells were analyzed for CD40L expression by flow cytometry. Anti-CD3 stimulation of PBMC resulted in a marked up-regulation of CD40L on CD4$^+$ T cells from 2 to 6 h, but CT treatment resulted in >50% reduction (p<0.05) in the mean level of CD40L expression at all time periods (Table 4). In contrast, the addition of LT-IIa or LT-IIb to anti-CD3 stimulated PBMC minimally affected the mean level of CD40L expression compared to anti-CD3 controls (Table 4).

TABLE 4

Effects of CT, LT-IIa, or LT-IIb on CD40L expression by human PBMC

| Stimulant | Toxin (100 ng/ml) | CD40L % +ve cells at: 2 h | 4 h | 6 h | 24 h |
|---|---|---|---|---|---|
| None | — | 1.81 ± 0.93 | 2.24 ± 1.27 | 1.16 ± 0.64 | 1.32 ± 0.47 |
| anti-CD3 | — | 28.39 ± 7.49 | 37.41 ± 9.21 | 33.18 ± 8.77 | 5.35 ± 3.88 |
| anti-CD3 | CT | *11.06 ± 3.94 | *15.41 ± 5.57 | *14.22 ± 4.69 | 2.88 ± 1.31 |
| anti-CD3 | LT-IIa | 27.61 ± 6.08 | 35.68 ± 4.49 | 32.15 ± 6.77 | 5.19 ± 3.35 |
| anti-CD3 | LT-IIb | 23.83 ± 4.12 | 33.19 ± 6.27 | 31.59 ± 4.13 | 4.93 ± 2.17 |

The data represent the mean ± SD of cultures derived from 4 donors.
*indicates significant differences at p < 0.05 compared to anti-CD3 treated PBMC.

To determine if the observed difference in CD40L expression was due to a direct effect of CT, LT-IIa, or LT-IIb on CD4$^+$ T cells, purified CD4$^+$ T cells were stimulated with plate-bound anti-CD3 with or without the toxins and then analyzed by flow cytometry for CD40L expression. Anti-CD3 stimulated CD4$^+$ T cells again showed a marked up-regulation of CD40L that reached maximal levels at 6 h, and the addition of CT resulted in a significant (~50%) reduction (p<0.05) in CD40L expression at 2, 4, and 6 hr (FIG. 7). In contrast, CD4+ T cells cultured with LT-IIa or LT-IIb exhibited <15% reduction ($p>0.05$). in the mean level of CD40L expression between 2 and 24 h (FIG. 7). No significant differences were observed in cell viability as revealed by trypan blue exclusion between CT-, LT-IIa-, and LT-IIb-treated CD4+ T cells (data not shown). Thus CT has a direct suppressive effect on the up-regulation of CD40L in CD4+ T cells.

EXAMPLE 19

CT- but not LT-IIa- or LT-IIb-treated CD4+ T Cells Suppressed CD40-CD40L-Dependent TNF-α and IL-12p70 Production by Monocytes and Dendritic Cells Because of the importance of CD40-CD40L interactions in the production of IL-12, the functional significance of the effects of the toxins on CD40L expression was examined by co-culturing toxin-treated CD4+ T cells with APC and analyzing TNF-α and IL-12 p70 production. For this purpose, CD4+ T cells were stimulated with plate-bound anti-CD3 in the presence or absence of the toxins for 6 hr, washed, fixed with paraformaldehyde, and then co-cultured with autologous monocytes or monocyte-derived dendritic cells. After 48 h incubation, cell-free supernatants were analyzed for TNF-α and IL-12 p70 production by ELISA. To determine whether CD40L was involved in the production of these cytokines, the co-culture was also carried out in the presence of anti-CD40L mAb or an isotype control Ab.

Treatment of anti-CD3-stimulated CD4+ T cells with CT resulted in a significant reduction in TNF-α and IL-12 production by monocytes and dendritic cell, whereas neither LT-IIa- or LT-IIb-treated CD4+ T cells, resulted in any significant reduction in the synthesis of IL-12 production by the APC (FIG. 8). The addition of anti-CD40L mAb to CT-treated co-cultures resulted in a further reduction in TNF-α and IL-12 production (FIG. 8). Thus, although CT-treated co-cultures produced significantly less IL-12 production from monocytes and dendritic cells compared to anti-CD3 controls, CT did not completely abrogate CD40L-dependent IL-12 p70 or TNF-α production (FIG. 8). The addition of anti-CD40L mAb to LT-IIa or LT-IIb-treated co-cultures significantly inhibited both TNF-α and IL-12 production from autologous monocytes and dendritic cells (FIG. 8). Thus, the action of CT on CD4+ T cells led to the suppression of CD40-dependent TNF-α and IL-12 production in both monocytes and dendritic cells. In contrast, LT-IIa- and LT-IIb-treated CD4+ T cells were more able to stimulate cytokine production from APC through CD40-dependent interactions.

Discussion

It was previously reported that CT, LT-IIa, and LT-IIb exhibited potent but distinct adjuvant responses in mice (45), and that CT and the type II HLT induced discrete Th cytokine production and IgG subclass responses. In the present study, it is shown that CT and the type II HLT have similar differential effects on anti-CD3-stimulated human PBMC, and this system is used to investigate the mechanisms responsible for these differences. The results showed that CT, LT-IIa, and LT-IIb differentially affected CD4+ T cell activation and CD40-dependent cytokine production: CT, but not LT-IIa or LT-IIb, significantly suppressed the level of CD40L expression on anti-CD3 stimulated CD4+ T cells. Furthermore, CT-treated CD4+ T cells induced significantly less CD40-dependent IL-12 p70 production in both monocytes and monocyte-derived dendritic cells than either LT-IIa- or LT-IIb-treated CD4+ T cells.

Analysis of holotoxin-treated PBMC suggested that CT exhibited distinct suppressive effects on CD4+ T cells that were not apparent with LT-IIa- or LT-IIb- treated cultures. The observations that CT reduced T cell activation markers on anti-CD3 stimulated CD4+ T cells are in agreement with previous studies, but the present study showed that neither LT-IIa or LT-IIb significantly suppressed CD25 or CD69 expression on CD4+ T. These differences were further supported by the significant reduction in T cell proliferation and CD40L expression in CT-treated cultures. The up-regulation of CD40L on human T cells has been shown to depend upon both IL-2 and IL-12 production. Moreover, previously activated T cells could up-regulate CD40L in the presence of IL-2 and without anti-CD3 stimulation. Thus, the differential inhibition of CD25 as well as IL-2 and IL-12 production by CT and the type II HLT may, in part, explain the observed levels of CD40L expression in CT-, LT-IIa-, and LT-IIb-treated cultures.

The differentiation of naive Th cells into Th1 and Th2 cells is governed by IL-12 and IL-4, respectively, and so are their ability to activate specific signal transducer and activator of transcription (STAT) molecules. The ability of CT to act as a mucosal adjuvant has been well studied and has typically been classified as an adjuvant inducing Th2-associated immune responses. Several studies, including data presented herein, demonstrate that CT can directly or indirectly down-regulate IL-12 production from APC. Conversely, while CT does possess inhibitory properties for the induction of Th1 cytokines, its mucosal adjuvanticity has been shown to be strongly dependent upon Th2 cytokines, especially IL-4. Moreover, CT appears to directly inhibit Th1 clones but does not possess these inhibitory effects on Th2 clones producing IL-4. The data presented in this study defines an additional pathway by which HLT affect IL-12 production from APC. The type II HLT did not suppress the up-regulation of CD40L or CD40-dependent IL-12 production from autolgous APC compared to the levels observed with CT-treated cultures. Th cells able to differentiate into Th1 or Th2 cells have been found to polarize predominantly into the Th2 phenotype when primed under conditions containing both IL-4 and IL-12 compared to conditions containing only IL-12. However, in the presence of a higher IL-12 dose, the number of IL-4 producing cells observed when priming in the presence of IL-4 and IL-12 was reduced by almost half while there was a concomitant rise in the number of INF-γ producing cells. Considering that anti-CD3 stimulated PBMC cultures produced similar levels of IL-4, the ability of CT and the type II HLT to alter the levels of IL-12 produced during Th cell activation and priming further explain the distinct Th profiles observed when these HLT are used as adjuvant.

The ability of APCs and T cells to deliver mutual co-stimulatory signals during an immune response is necessary for the development of effector cells. Among these circumstances, the CD40-CD40L pathway has diverse effects (50,51,57). Up-regulation of CD40L upon T cell activation has been implicated as a primary mechanism responsible for the induction of IL-12 and Th1 responses. Th1 responses are deficient in the absence of CD40-CD40L interactions, and CD40L-deficient T cells are defective in IFN-γ production while conversely exhibiting higher IL-4 production than normal cells (56). Moreover, the inability of CD40L-deficient T cells to differentiate into Th1 effector cells was due to a lack of IL-12 production from APC. These findings are consistent with the present observations concerning the abilities of CT, LT-IIa, and LT-IIb to differentially affect CD40L expression on CD4+ T cells and subsequent Th1 and Th2 cytokine production.

Dendritic cells (DC) are believed to be the major APC involved in the primary immune response. Mature DC have been shown to express an array of co-stimulatory molecules and thus are potent stimulators of both T and B lymphocytes. An important final step in the development of DC from an immature phagocytic DC to a mature DC capable of priming naive T cells involves signaling through CD40, and the CD40-CD40L interaction promotes the ability of DC to efficiently stimulate CD8+ CTL responses (58,59). Despite previous studies demonstrating the ability of CT to induce a predominant Th2-associated immune response, as well as its potent inhibitory effects on IL-12 production from APC, several groups have demonstrated the ability of CT to induce IL-12-dependent CTL responses in mice (60). Thus, although CT has been shown to reduce IL-12 production from monocytes and DC, as well as suppress CD40L-dependent IL-12 production from APC, CT did not abrogate IL-12 production. The present study showed that CT-treated CD4$^+$ T cells expressed significantly higher levels of CD40L than non-stimulated CD4$^+$ cultures and these cells were still capable of inducing IL-12 p70 production from both monocytes and monocyte derived dendritic cells. However, due to the differences in CD40L expression and IL-12 production induced by CT and the type II HLT, their use as adjuvants may permit the selective generation of predominantly antibody-mediated or cell-mediated immunity.

In summary, the present study indicates that CT, LT-IIa, and LT-IIb induced different Th cell profiles from anti-CD3 stimulated PBMC cultures. By directly comparing these HLT, the present study demonstrates CT, LT-IIa, and LT-IIb possess unique immunomodulatory properties on CD4$^+$ T cells that accounted, in part, for their observed cytokine differences.

The following references were cited herein:
1. Clements et al. 1988. *Vaccine* 6: 269.
2. Elson. 1987. *Fed. Proc.* 46: 1778.
3. Spangler. 1992. *Microbiol. Rev.* 56: 622.
4. Lycke et al. 1992. *Eur. J. Immunol.* 22: 2277.
5. Holmgren. 1981. *Nature* 292: 413.
6. Wilson et al. 1990. *Scand. J. Immunol.* 31: 443.
7. Tamura et al. 1994. *Vaccine* 12: 1238.
8. Nashar et al. 1996. *Proc. Natl. Acad. Sci. USA* 93: 226.
9. Yamamoto et al. 1999. *J. Immunolgy* 162: 7015.
10. Nashar et al. 1997. *Immunology* 91: 572.
11. Holmes et al. 1995. Cholera toxin and related enterotoxins of gram negative bacteria. In *Handbook of Natural Toxins*. J. Moss, B. Iglewski, M. Vaughn, and A. T. Tu, eds. MarcelDekker, inc., New York, p. 225.
12. Pickett et al. 1986. *J. Bacteriol.* 165: 348.
13. Honda et al. 1981. *Infect. Immun.* 34: 337.
14. Green et al. 1983. *Infect. Immun.* 41: 383.
15. Guth et al. 1986. *Infect. Immun.* 54: 529.
16. Guth et al. 1986. *Infect. Immun.* 54: 587.
17. Holmes et al. 1990. The *Escherichia coli/Vibrio cholerae* family of enterotoxins. Symposium on Molecular Mode of Action of Selected Microbial Toxins in Foods and Feeds. In A. E. Pohland, V. R. Dowell, and J. L. Richard, eds. Plenum Press, New York, p. 91.
18. Pickett et al. 1987. *J. Bacteriol.* 169: 5180.
19. Pickett et al. 1989. *J. Bact.* 171: 4945.
20. Fukuta et al. 1988. *Infect. Immun.* 56: 1748.
21. Martin et al. 2000. *Infect. Immun.* 68: 281.
22. Wu and Russell. 1998. *Vaccine* 16: 286.
23. Czerkinsky et al. 1989. *Infect. Immun.* 57: 1072.
24. Hajishengallis et al. 1995. *J. Immunol.* 154: 4322.
25. Jobling and Holmes. 1992. *Infect. Immun.* 60: 4915.
26. Connell and Holmes. 1992. *Infect. Immun.* 60: 1653.
27. Connell and Holmes. 1992. *Infect. Immun.* 60: 63.
28. Svennerholm and Holmgren. 1978. *Curr. Microbiol.* 1: 19.
29. June et al. 1994. *Immunology Today* 15: 321.
30. Lenschow et al. 1996. *Annu. Rev. Immunol.* 14: 233.
31. Cong et al. 1997. *J. Immunol.* 159: 5301.
32. Agren et al. 1997. *J. Immunol.* 158: 3936.
33. DeBenedette et al. 1995. *J. Exp. Med.* 181: 985.
34. Freeman et al. 1995. *Immunity* 2: 523.
35. Thompson. 1995. *Cell* 81: 979.
36. Paul. 1987. *FASEB J.* 1: 456.
37. Snapper et al. 1988. *J. Immunol.* 140: 2121.
38. Harokopakis et al. 1998. *Infect. Immun.* 66: 4299.
39. Nashar and Hirst. 1995. *Vaccine* 13: 803.
40. Hirabayashi et al. 1991. *Immunology* 72: 329.
41. Simons and Ikonen. 1997. *Nature* 387: 569.
42. Cheng et al. 1999. *J. Exp. Med.* 190: 1549.
43. Croft 1994. *Curr. Opin. Immunol.* 6: 431.
44. Liu et al. 1991. *Eur. J. Immunol.* 21: 2951.
45. Martin et al. 2000. *Infect. Immun.* 68:281–287.
46. Takahashi et al. 1996. *J. Infect. Dis.* 173:627–635.
47. Xu-Amano et al. 1993. *J. Exp. Med.* 178:1309–1320.
48. Yamamoto et al. 1997. *Proc. Natl. Acad. Sci. USA* 94:5267–5272.
49. Marinaro et al. 1995. *J. Immunol.* 155:4621–4629.
50. Banchereau et al. 1994. *Annu. Rev. Immunol.* 12:881–922.
51. Foy et al. 1996. *Annu. Rev. Immunol.* 14:591–617.
52. Shu et al. 1995. *Eur. J. Immunol.* 25:1125–1128.
53. Hsieh et al. 1993. *Science* 260:547–549.
54. Manetti et al. 1993. *J. Exp. Med.* 177:1199–1204.
55. Schmitt et al. 1994. *Eur. J. Immunol.* 24:343–347.
56. Howland et al. 2000. *J. Immunol.* 164:4465–4470.
57. van Kooten and Banchereau. 2000. *J. Leukoc. Biol.* 67:2–17.
58. Bennett et al. 1998. *Nature* 393:478–480.
59. Schoenberger et al. 1998. *Nature* 393:480–483.
60. Belyakov et al. 1998. *Proc. Natl. Acad. Sci. USA* 95:1709–1714.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of inducing an immune response, wherein the method comprises administering mucosally to a subject a recombinant immunogen comprising a fusion protein containing a heterologous antigen of interest fused to the A2 and B subunits of a type II heat-labile enterotoxin.

2. The method of claim 1, wherein said antigen of interest is salivary binding protein (SBR) from *Streptococcus mutans* surface protein (Ag I/II).

3. The method of claim 1, wherein said type II heat-labile enterotoxin is selected from the group consisting of *E. coil* heat-labile type IIa toxin and *E. coil* heat-labile type IIb toxin.

4. The method of claim 1, wherein said immunogen is administered by a route selected from the group consisting of orally, intranasally, intrarectally, and intravaginally.

5. A method of increasing Th1 response and cell-mediated immunity, wherein the method comprises administering mucosally to a subject a recombinant immunogen comprising a fusion protein containing a heterologous antigen of interest fused to the A2 and B subunits of a type II heat-labile enterotoxin.

6. The method of claim 5, wherein said antigen of interest is salivary binding protein (SBR) from *Streptococcus mutans* surface protein (Ag I/II).

7. The method of claim 5, wherein said immunogen is administered by a route selected from the group consisting of orally, intranasally, intrarectally, intravaginally.

8. A method of increasing Th1 response and cell-mediated immunity, wherein the method comprises administering mucosally to a subject a recombinant immunogen comprising a fusion protein containing a heterologous antigen of interest fused to the A2 and B subunits of a *E. Coil* heat-labile enterotoxin.

9. The method of claim 8, wherein said antigen of interest is salivary binding protein (SBR) from *Streptococcus mutans* surface protein (Ag I/II).

10. The method of claim 8, wherein said immunogen is administered by a route selected from the group consisting of orally, intranasally, intrarectally, intravaginally.

* * * * *

SEQUENCE LISTING

```
<160> NUMBER OF SEQ ID NOS: 2

<210> SEQ ID NO 1
<211> LENGTH: 20
<212> TYPE: DNA
<213> ORGANISM: Unknown
<220> FEATURE:
<221> NAME/KEY: primer_bind
<223> OTHER INFORMATION: primer to amplify a fragment encoding LT-IIa
      A2 domain and the B polypeptide from pTDC2000

<400> SEQUENCE: 1
gtaaaacgac ggccagtgag

<210> SEQ ID NO 2
<211> LENGTH: 21
<212> TYPE: DNA
<213> ORGANISM: Unknown
<220> FEATURE:
<221> NAME/KEY: primer_bind
<223> OTHER INFORMATION: primer to amplify a fragment encoding LT-IIa
      A2 domain and the B polypeptide from pTDC2000

<400> SEQUENCE: 2
gtaacctcga ggcctggaga g
```